(12) United States Patent
Burnett et al.

(10) Patent No.: US 9,931,122 B2
(45) Date of Patent: Apr. 3, 2018

(54) GASTRIC RETAINING DEVICES AND METHODS

(71) Applicant: BAROnova, Inc., San Carlos, CA (US)

(72) Inventors: Daniel R. Burnett, San Francisco, CA (US); Gregory W. Hall, Redwood City, CA (US)

(73) Assignee: BAROnova, Inc., San Carlos, CA (US)

( * ) Notice: Subject to any disclaimer, the term of this patent is extended or adjusted under 35 U.S.C. 154(b) by 96 days.

(21) Appl. No.: 14/618,868

(22) Filed: Feb. 10, 2015

(65) Prior Publication Data

US 2015/0150561 A1    Jun. 4, 2015

Related U.S. Application Data

(63) Continuation of application No. 12/434,594, filed on May 1, 2009, which is a continuation of application
(Continued)

(51) Int. Cl.
*A61B 17/12*    (2006.01)
*A61B 5/145*    (2006.01)
(Continued)

(52) U.S. Cl.
CPC .... *A61B 17/12099* (2013.01); *A61B 5/14539* (2013.01); *A61B 17/1219* (2013.01); *A61B 17/12022* (2013.01); *A61B 17/12136* (2013.01); *A61B 17/12172* (2013.01); *A61F 5/003* (2013.01); *A61F 5/0036* (2013.01);
(Continued)

(58) Field of Classification Search
CPC ........ A61B 17/12099; A61B 17/12022; A61B 17/12136; A61B 17/12172; A61B 17/1219; A61B 5/14539; A61B 2017/00893; A61B 17/12177; A61B 2017/12054; A61B 2017/12086; A61B 2017/00867; A61B 2017/00818; A61F 5/0036; A61F 5/0079; A61F 5/003
See application file for complete search history.

(56) References Cited

U.S. PATENT DOCUMENTS 2,499,045 A    2/1950  Ray et al.
3,154,077 A    10/1964 Cannon
(Continued)

FOREIGN PATENT DOCUMENTS

DE    4012642    10/1991
JP    2010-537790    12/2010
(Continued)

*Primary Examiner* — Julian W Woo
(74) *Attorney, Agent, or Firm* — Levine Bagade Han LLP

(57) ABSTRACT

Methods, devices and systems facilitate gastric retention of a variety of therapeutic devices. devices generally include a support portion for preventing the device from passing through the pyloric valve or esophagus wherein a retaining member may optionally be included on the distal end of the positioning member for further maintaining a position of the device in the stomach. Some embodiments are deliverable into the stomach through the esophagus, either by swallowing or through a delivery tube or catheter. Some embodiments are fully reversible. Some embodiments self-expand within the stomach, while others are inflated or otherwise expanded.

16 Claims, 28 Drawing Sheets

Related U.S. Application Data

No. 11/215,430, filed on Aug. 29, 2005, which is a continuation-in-part of application No. 10/833,950, filed on Apr. 27, 2004, now Pat. No. 8,048,169, and a continuation-in-part of application No. 10/671,191, filed on Sep. 24, 2003, now Pat. No. 6,994,095.

(60) Provisional application No. 60/525,105, filed on Nov. 26, 2003, provisional application No. 60/490,421, filed on Jul. 28, 2003.

(51) Int. Cl.
  *A61F 5/00* (2006.01)
  *A61B 5/03* (2006.01)
  *A61B 5/07* (2006.01)
  *A61B 17/00* (2006.01)

(52) U.S. Cl.
  CPC ............ *A61F 5/0079* (2013.01); *A61B 5/036* (2013.01); *A61B 5/073* (2013.01); *A61B 17/12177* (2013.01); *A61B 2017/00818* (2013.01); *A61B 2017/00867* (2013.01); *A61B 2017/00893* (2013.01); *A61B 2017/1205* (2013.01); *A61B 2017/12054* (2013.01); *A61B 2017/12086* (2013.01)

(56) References Cited

U.S. PATENT DOCUMENTS

| | | |
|---|---|---|
| 3,915,171 A | 10/1975 | Shermeta |
| 4,057,065 A * | 11/1977 | Thow .................... A61M 25/10 604/101.05 |
| 4,133,315 A | 1/1979 | Berman et al. |
| 4,240,412 A | 12/1980 | James |
| 4,246,893 A | 1/1981 | Berson |
| 4,311,146 A * | 1/1982 | Wonder ........... A61B 17/12109 264/264 |
| 4,315,509 A | 2/1982 | Smit |
| 4,341,218 A * | 7/1982 | U ..................... A61B 17/12099 604/907 |
| 4,368,739 A | 1/1983 | Nelson |
| 4,416,267 A | 11/1983 | Garren et al. |
| 4,485,805 A | 12/1984 | Foster, Jr. |
| 4,517,979 A | 5/1985 | Pecenka |
| 4,598,699 A | 7/1986 | Garren et al. |
| 4,648,383 A | 3/1987 | Angelchik |
| 4,657,020 A | 4/1987 | Lifton |
| 4,694,827 A | 9/1987 | Weiner et al. |
| 4,735,214 A | 4/1988 | Berman |
| 4,762,128 A | 8/1988 | Rosenbluth |
| 4,836,204 A | 6/1989 | Landymore et al. |
| 4,878,905 A | 11/1989 | Blass |
| 4,925,446 A * | 5/1990 | Garay .................... A61F 5/003 128/899 |
| 4,930,496 A | 6/1990 | Bosley |
| 4,946,440 A | 8/1990 | Hall |
| 5,011,488 A | 4/1991 | Ginsburg |
| 5,108,420 A | 4/1992 | Marks |
| 5,129,915 A | 7/1992 | Cantenys |
| 5,192,301 A | 3/1993 | Kamiya et al. |
| 5,234,454 A * | 8/1993 | Bangs .................... A61F 5/003 604/101.05 |
| 5,246,445 A | 9/1993 | Yachia et al. |
| 5,282,829 A | 2/1994 | Hermes |
| 5,306,300 A | 4/1994 | Berry |
| 5,312,343 A | 5/1994 | Krog et al. |
| 5,423,872 A | 6/1995 | Cigaina |
| 5,509,888 A | 4/1996 | Miller |
| 5,514,091 A | 5/1996 | Yoon |
| 5,514,178 A | 5/1996 | Torchio |
| 5,540,701 A | 7/1996 | Sharkey et al. |
| 5,545,210 A | 8/1996 | Hess et al. |
| 5,634,936 A | 6/1997 | Linden et al. |
| 5,674,192 A | 10/1997 | Sahatjian et al. |
| 5,676,688 A | 10/1997 | Jaker et al. |
| 5,707,355 A | 1/1998 | Zimmon |
| 5,750,585 A | 5/1998 | Park et al. |
| 5,752,971 A | 5/1998 | Rosenbluth et al. |
| 5,782,800 A | 7/1998 | Yoon |
| 5,820,584 A | 10/1998 | Crabb |
| 5,853,422 A | 12/1998 | Huebsch et al. |
| 5,947,991 A | 9/1999 | Cowan |
| 5,976,174 A | 11/1999 | Ruiz |
| 6,067,991 A | 5/2000 | Forsell |
| 6,102,928 A | 8/2000 | Bonutti |
| 6,112,703 A | 9/2000 | Handelsman |
| 6,117,159 A | 9/2000 | Huebsch et al. |
| 6,152,144 A | 11/2000 | Lesh et al. |
| 6,159,219 A | 12/2000 | Ren |
| 6,162,201 A | 12/2000 | Cohen |
| 6,183,520 B1 | 2/2001 | Pintauro et al. |
| 6,245,090 B1 | 6/2001 | Gilson et al. |
| 6,270,515 B1 | 8/2001 | Linden et al. |
| 6,371,974 B1 | 4/2002 | Brenneman et al. |
| 6,409,656 B1 | 6/2002 | Sangouard et al. |
| 6,454,785 B2 | 9/2002 | De Hoyos Garza |
| 6,488,962 B1 | 12/2002 | Berner et al. |
| 6,503,264 B1 | 1/2003 | Birk |
| 6,527,701 B1 | 3/2003 | Sayet et al. |
| 6,527,739 B1 | 3/2003 | Bigus et al. |
| 6,540,789 B1 | 4/2003 | Silverman et al. |
| 6,544,291 B2 | 4/2003 | Taylor |
| 6,558,400 B2 | 5/2003 | Deem et al. |
| 6,579,301 B1 | 6/2003 | Bales et al. |
| 6,600,953 B2 | 7/2003 | Flesler et al. |
| 6,652,578 B2 | 11/2003 | Bailey et al. |
| 6,675,809 B2 | 1/2004 | Stack et al. |
| 6,689,046 B2 | 2/2004 | Sayet et al. |
| 6,702,846 B2 | 3/2004 | Mikus |
| 6,740,121 B2 | 5/2004 | Geitz |
| 6,755,869 B2 | 6/2004 | Geitz |
| 6,802,868 B2 | 10/2004 | Silverman et al. |
| 6,860,895 B1 | 3/2005 | Akerfeldt et al. |
| 6,994,095 B2 | 2/2006 | Burnett |
| 7,011,621 B2 | 3/2006 | Sayet et al. |
| 7,037,344 B2 | 5/2006 | Kagan et al. |
| 7,054,690 B2 | 5/2006 | Imran et al. |
| 7,087,072 B2 | 8/2006 | Marino et al. |
| 7,120,498 B2 | 10/2006 | Imran et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,160,312 B2 | 1/2007 | Saadat |
| 7,167,750 B2 | 1/2007 | Knudson et al. |
| 7,186,251 B2 | 3/2007 | Malecki et al. |
| 7,291,160 B2 * | 11/2007 | DeLegge ................. A61F 5/004 604/909 |
| 7,320,696 B2 | 1/2008 | Gazi et al. |
| 7,588,584 B2 | 9/2009 | Fogarty et al. |
| 7,842,053 B2 | 11/2010 | Chanduszko et al. |
| 8,048,169 B2 | 11/2011 | Burnett et al. |
| 8,257,389 B2 | 9/2012 | Chanduszko et al. |
| 2002/0013601 A1 | 1/2002 | Nobles et al. |
| 2002/0038100 A1 | 3/2002 | Okada |
| 2002/0091395 A1 | 7/2002 | Gabbay |
| 2002/0161341 A1 | 10/2002 | Stinson et al. |
| 2002/0165589 A1 | 11/2002 | Imran et al. |
| 2002/0188354 A1 | 12/2002 | Peghini |
| 2002/0198470 A1 | 12/2002 | Imran et al. |
| 2002/0198479 A1 | 12/2002 | Talish |
| 2003/0023150 A1 | 1/2003 | Yokoi et al. |
| 2003/0040804 A1 | 2/2003 | Stack et al. |
| 2003/0078611 A1 | 4/2003 | Hashiba et al. |
| 2003/0093117 A1 | 5/2003 | Saadat |
| 2003/0109931 A1 | 6/2003 | Geitz |
| 2003/0109935 A1 | 6/2003 | Geitz |
| 2003/0120328 A1 | 6/2003 | Jenkins et al. |
| 2003/0144708 A1 | 7/2003 | Starkebaum |
| 2003/0152601 A1 | 8/2003 | Kanayama |
| 2003/0153806 A1 | 8/2003 | Miller |
| 2003/0158601 A1 | 8/2003 | Silverman et al. |
| 2004/0034408 A1 | 2/2004 | Majercack |

(56) References Cited

U.S. PATENT DOCUMENTS

| | | |
|---|---|---|
| 2004/0059368 A1 | 3/2004 | Maryanka |
| 2004/0107004 A1 | 6/2004 | Levine et al. |
| 2004/0117031 A1 | 6/2004 | Stack et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0213825 A1 | 10/2004 | Levy |
| 2004/0230222 A1 | 11/2004 | van der Burg et al. |
| 2004/0236357 A1 | 11/2004 | Kraemer et al. |
| 2004/0267378 A1 | 12/2004 | Gazi et al. |
| 2005/0033331 A1 | 2/2005 | Burnett et al. |
| 2005/0033332 A1 | 2/2005 | Burnett |
| 2005/0038460 A1 | 2/2005 | Jayaraman |
| 2005/0038470 A1 | 2/2005 | Van Der Burg et al. |
| 2005/0055039 A1 | 3/2005 | Burnett et al. |
| 2005/0064009 A1 | 3/2005 | Bates |
| 2005/0090873 A1 | 4/2005 | Imran et al. |
| 2005/0096673 A1 | 5/2005 | Stack et al. |
| 2005/0149142 A1 | 7/2005 | Starkebaum |
| 2005/0192627 A1 | 9/2005 | Whisenant et al. |
| 2005/0192629 A1 | 9/2005 | Saadat et al. |
| 2005/0273060 A1 | 12/2005 | Levy et al. |
| 2005/0288786 A1 | 12/2005 | Chanduszko |
| 2006/0020278 A1 | 1/2006 | Burnett et al. |
| 2006/0178691 A1 | 8/2006 | Binmoeller |
| 2006/0217763 A1 | 9/2006 | Abbott et al. |
| 2006/0259074 A1 | 11/2006 | Kelleher et al. |
| 2006/0282107 A1 | 12/2006 | Hashiba et al. |
| 2006/0293742 A1 | 12/2006 | Dann et al. |
| 2007/0016262 A1 | 1/2007 | Gross et al. |
| 2007/0027548 A1 | 2/2007 | Levine et al. |
| 2007/0056591 A1 | 3/2007 | McSwain |
| 2007/0083224 A1 | 4/2007 | Hively |
| 2007/0135831 A1 | 6/2007 | Burnett et al. |
| 2007/0178160 A1 | 8/2007 | Burnett |
| 2007/0198082 A1 | 8/2007 | Kapadia et al. |
| 2007/0239284 A1 | 10/2007 | Skerven et al. |
| 2007/0250132 A1 | 10/2007 | Burnett |
| 2009/0118757 A1 | 5/2009 | Burnett et al. |
| 2009/0118758 A1 | 5/2009 | Burnett et al. |
| 2009/0177288 A1 | 7/2009 | Wallsten |
| 2009/0182357 A1 | 7/2009 | Burnett et al. |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0198210 A1 | 8/2009 | Burnett et al. |
| 2009/0216262 A1 | 8/2009 | Burnett et al. |
| 2009/0299486 A1 | 12/2009 | Shohat et al. |

FOREIGN PATENT DOCUMENTS

| | | |
|---|---|---|
| WO | WO 88/00027 | 1/1988 |
| WO | WO 90/00369 | 1/1990 |
| WO | WO 00/48672 | 8/2000 |
| WO | WO 02/091961 | 11/2002 |
| WO | WO 03/017882 | 3/2003 |
| WO | WO 2005/009288 | 2/2005 |
| WO | WO 2005/104989 | 10/2005 |
| WO | WO 2006/020370 | 2/2006 |
| WO | WO 2006/135857 | 12/2006 |
| WO | WO 2007/027812 | 3/2007 |
| WO | WO 2007/092390 | 8/2007 |
| WO | WO 2007/092501 | 8/2007 |
| WO | WO 2009/033049 | 3/2009 |

* cited by examiner

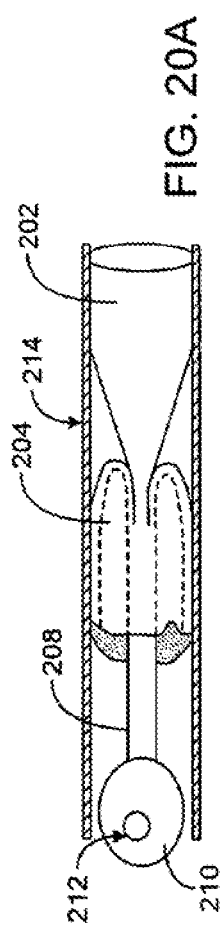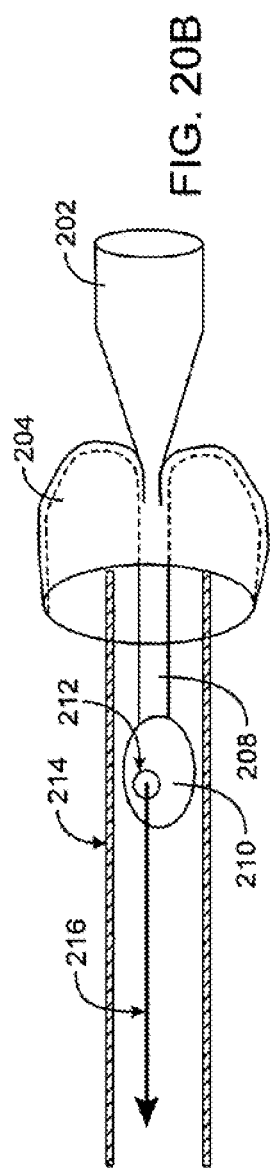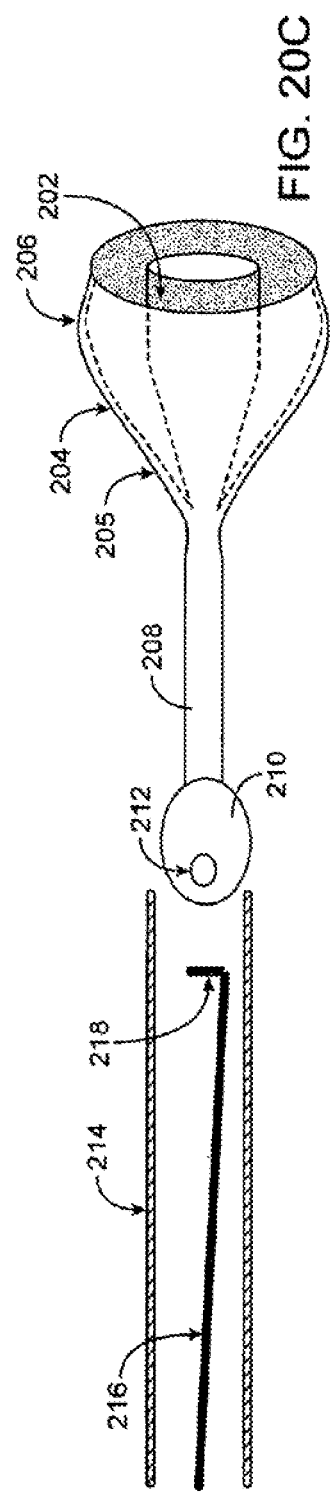

GASTRIC RETAINING DEVICES AND METHODS

CROSS-REFERENCE TO RELATED APPLICATIONS

This application is a continuation of U.S. patent application Ser. No. 12/434,594 filed May 1, 2009, which is a continuation of U.S. patent application Ser. No. 11/215,430, filed Aug. 29, 2005, which is a continuation-in-part of U.S. patent application Ser. No. 10/833,950, filed Apr. 27, 2004 (now U.S. Pat. No. 8,048,169, issued Nov. 1, 2011), which claims the benefit of U.S. Provisional Patent Application Ser. No. 60/525,105, filed Nov. 26, 2003, and which is a continuation-in-part of U.S. patent application Ser. No. 10/671,191, filed Sep. 24, 2003 (now U.S. Pat. No. 6,994,095, issued Feb. 7, 2006), which claims the benefit of U.S. Provisional Patent Application Ser. No. 60/490,421, filed Jul. 28, 2003, the contents of which are incorporated herein by reference in their entirety.

BACKGROUND OF THE INVENTION

Field of the Invention

The present invention relates generally to medical devices and methods. More specifically, the invention relates to devices and methods for partially and/or intermittently obstructing a pyloric valve to decrease gastric emptying, such as for treating obesity.

Obesity has become a medical problem of epidemic proportions in the United States. Recent governmental studies estimate that as many as 40% of Americans are obese (defined as a Body Mass Index over 30), and of those, almost 20% are morbidly obese. Unfortunately, there is no indication that these percentages will decrease and every indication that they will increase in the coming years. Studies have linked obesity to countless health risks, a small sampling of which includes cardiovascular disease, cancer, diabetes, orthopedic injuries and complaints, obstructive sleep apnea, chronic fatigue and depression. Despite billions of dollars spent searching for obesity cures, conducting research into nutrition and exercise, and educating the public about obesity, efforts to date have been largely ineffective.

Many Americans have tried combating obesity with diet, exercise and even medications, to no avail. Most people who lose weight through diet and exercise gain it back again in a short period of time. Available medications can have serious side effects, as was evidenced by the recent scare with the Fen-Phen dietary medication. Faced with the difficulty of diet and exercise, nutritional information that seems to change radically and rapidly, and diet medications and supplements that typically do not work and may cause serious side effects, many obese people become frustrated and either decide to remain obese or choose to pursue a more drastic treatment option.

The more drastic options typically involve surgical procedures, such as stomach stapling, other gastric reduction surgical techniques, placement of a constrictive band around the outside of the stomach, and gastric bypass. The most well known procedure, in part due to well-publicized experiences of celebrities like Al Roker and Carney Wilson, is the gastric bypass operation, known technically as a Roux-En-Y gastric bypass. In this procedure, the stomach is actually bypassed, and a very small stomach-like pouch remains, making a patient feel full after ingesting a small amount of food. Although gastric bypass can be highly effective, it is acknowledged to be a very high-risk operation, with a 1-2% mortality rate, a number of possible complications such as digestive problems, and a recovery period of up to 6 months. The other surgical alternatives are also associated with either high risk, low rate of effectiveness, or both.

Stemming from the high risks of gastric surgical procedures and the ineffectiveness of diet and exercise for many obese people, a number of medical devices have been developed to address weight loss and obesity, but these too have numerous drawbacks. Some devices, for example, try to bypass a portion of the stomach or small intestine by essentially creating a tube or chute through which food passes without any nutrients or calories being absorbed. Such devices are described, for example, in U.S. Pat. No. 5,820,584 and U.S. Patent Application Publication Nos. 2003/0040804 and 2003/0109931. Unfortunately, these are designed to cause absorption problems in a patient, which may reduce intake of calories into the body but which also typically leads to "dumping" of food too rapidly through the digestive tract, leading to numerous gastrointestinal symptoms.

Another approach, as described for example in U.S. Patent Application Publication No. 2003/0093117, involves performing a minimally invasive surgical procedure on a stomach, typically to reduce its volume. The drawbacks with such approaches are that they are still relatively invasive and they are typically difficult or impossible to reverse.

Other techniques involve placing space-occupying balloons and other devices within the stomach to make the patient feel full after eating small amounts of food. One such a device, for example, is described in U.S. Patent Application Publication No. 2003/0109935. Space occupying devices by themselves, however, may not be as effective as other treatments, and many currently available devices have an unacceptably serious risk of collapsing, passing through the stomach, and lodging somewhere in the intestines, thus causing a serious and potentially fatal intestinal blockage.

Yet another technique that has been attempted for treating obesity involves slowing down the rate at which food passes from the stomach, through the pyloric valve at the distal end of the stomach, and into the duodenum—i.e., the first part of the small intestine. Some researchers have found, for example, that stimulation of the gastric vagus nerve may result in reduced gastric motility leading to a loss of over 20% of excess weight in a nine month period. In another approach, severing the gastric vagus nerve may also be effective in treating obesity. These therapies, however, require invasive, sometimes irreversible, surgical procedures, and may have adverse effects on the ability of the vagus nerve to perform other important functions.

Others have tried slowing gastric emptying by placing implants or injecting bulking agents into tissue at or immediately adjacent the pyloric valve. Such techniques are described, for example, in U.S. Pat. No. 6,540,789 and U.S. Patent Application Publication Nos. 2003/0153806 and 2003/0158601. In general, such methods have not been found to be effective and, again, are often irreversible.

Therefore, because obesity is such an endemic and serious health problem, and because currently available treatment options are often ineffective, extremely risky or both, a need exists for effective, relatively non-invasive treatments for obesity. Ideally, such treatments would be relatively easy to use and deploy in a patient and would help treat obesity without a high risk of side effects or severe complications. Such treatments would also ideally be reversible. At least some of these objectives will be met by the present invention.

SUMMARY OF THE INVENTION

The present invention provides devices, methods and systems for obstructing or occluding a pyloric valve to provide weight loss and in some cases treat or ameliorate obesity. Devices are generally delivered into the stomach where they expand or are expanded to partially and/or intermittently obstruct or occlude the pyloric valve. By partially or intermittently obstructing or occluding the pyloric valve, contents of the stomach (i.e., food) are retained longer in the stomach, thus causing a patient to feel full sooner and longer, and thus leading to reduced food intake and to weight loss.

A device is generally configured such that, upon placement in the stomach, it moves naturally to the pyloric valve and contacts tissue adjacent the valve to obstruct the valve opening. A portion of the device is configured to assure that the device cannot pass through the pyloric valve and into the intestine, while another portion of the device is configured to contact stomach tissue adjacent the pyloric valve without damaging the tissue. During digestion and the natural contractions of the stomach, the device moves in and out of contact with the valve such that gastric contents are allowed to pass through to the small intestine, but the rate of passage is slowed. In a number of embodiments, a device may be introduced into the stomach either through a catheter device extending through the esophagus or by a patient swallowing the device. In some embodiments, the device may be retrieved and removed through the esophagus, often using the same device that was used for delivery. In other embodiments the obstructing device may dissolve over time and pass harmlessly through the digestive tract. In still further embodiments, the device is constructed as a retaining rather than an obstructing device, retaining a functional component such as gastric volume displacement component, a drug delivery component, or a gastric stimulator in the stomach while still allowing fluid to pass through the stomach and the pylorus.

In one aspect of the present invention, a device for obstructing a pyloric valve of a stomach includes an expandable support portion adapted to expand in the stomach from a first configuration to a larger second configuration, and a compliant tissue engagement portion coupled with the expandable support portion and adapted to engage stomach tissue adjacent the pyloric valve to at least intermittently obstruct the pyloric valve. In the second configuration, the support portion prevents passage of the device through the pyloric valve. In general, the support portion and the tissue engagement portion may have any of a number of different configurations. In one embodiment, the two portions are part of one, unitary extrusion, with the support portion having a greater wall thickness than the tissue engagement portion and/or containing one or more support members, such as support rings, lattices, frames or the like. In other embodiments, the two portions may be separate pieces coupled together. The compliant tissue engagement portion generally is sufficiently compliant so as to prevent or avoid injury (such as erosion) of stomach tissue with which the device comes in contact.

In some embodiments, though not in all, the expandable support portion is self-expanding, thus including at least one self-expanding material. For example, the self-expanding material may include but is not limited to Nitinol, spring stainless steel or other shape-memory, super-elastic or spring-loaded materials. In some embodiments, the self-expanding material includes at least one support member, such as but not limited to one or more rings, coils, cages, struts, scaffolding, baskets, spokes or umbrellas. Such support members may be configured such that, once expanded, they prevent the device from collapsing and passing into the intestine. In some embodiments, the support portion includes one or more support members coupled with at least one material, such as of GORE-TEX®, silicone, polyurethane or polyethylene. The tissue engagement portion, in turn, may extend from the support portion and be made of the same or different material, such as those just listed.

In alternative embodiments, the self-expanding material may include a self-expanding foam disposed within the expandable support portion and possibly the tissue engagement portion as well. For example, the foam may comprise polyethylene foam, polyurethane foam, silicone foam or the like. Like the support members just described, the expandable foam helps prevent passage of the device through the pyloric valve. Optionally, in some embodiments, the self-expanding material expands upon contacting one or more substances naturally present in the stomach.

In some embodiments, the support portion and the tissue engagement portion comprise at least one of GORE-TEX®, silicone, polyurethane and polyethylene, with the wall thickness of the support portion being greater than the wall thickness of the tissue engagement portion. In such a device the support portion may also include one or more support members, such as Nitinol rings or the like. In some embodiments, the tissue engagement portion is adapted to temporarily form a seal with the pyloric valve upon contacting the tissue adjacent the valve, and the tissue engagement portion is sufficiently compliant to avoid causing damage to the tissue on contacting it.

In various embodiments, the obstruction device may have any suitable dimensions, configurations or the like. In one embodiment, for example, the support portion in the second configuration has a widest cross-sectional diameter of between 2.5 cm and 15 cm. The support portion and tissue engagement portion, in one embodiment, have a combined volume in the second configuration greater than 200 cc. This combined volume, in some embodiments, is sufficient to allow the device to act as a space occupying device (as well as a pyloric valve obstructing device) for treating obesity. In addition to its dimensions, the specific gravity or buoyancy of the device may enhance its ability to contact and obstruct the pyloric valve. In one embodiment, for example, the device has a specific gravity of between 0.25 and 4.0. Some embodiments may include one or more chambers for introducing a gas or fluid to adjust the buoyancy of the device, or other mechanisms for adjusting buoyancy.

As mentioned, the support portion and tissue engagement portion may have any suitable shape in various embodiments. In some embodiments, for example, the device may have an overall cross-sectional shape of a circle, ellipse, triangle, diamond, rectangle, square, star, combinations thereof or the like. In one embodiment, for example, the device may have an oblong or tubular shape. In some embodiments, the device is hollow, with one or more openings to allow passage of stomach contents in and out of the hollow portion. In another embodiment, the device is cone-shaped, with the tissue engagement portion disposed toward an apex of the cone and the support portion disposed toward a base of the cone. Another embodiment may be shaped like a cup. As will be described further below, a number of suitable alternatives are possible in various embodiments.

Some embodiments of the device also include a positioning member extending from the tissue engagement portion and having a shape adapted to pass at least partially through the pyloric valve to position the device over the pyloric valve. In one embodiment, the device further includes an inner plug and a compliant outer shell. The shell is movable from a first configuration in which it overlaps at least part of the positioning member to a second configuration in which it overlaps at least part of the plug. In this embodiment, the plug and a first portion of the shell in the second configuration act as the support portion, and a second portion of the shell in the second configuration acts as the tissue engagement portion. In one embodiment, the shell in the second configuration is generally cone-shaped. The outer shell may be made of any suitable material(s), but in one embodiment it comprises a material such as GORE-TEX®, silicone, polyurethane or polyethylene, with the wall thickness of the first portion being greater than the wall thickness of the second portion. The thicker first portion provides some of the support function, while the thinner second portion provides the tissue engagement function. In some embodiments, the outer shell is movable from the first configuration to the second configuration by applying force to the shell with a distal end of an elongate catheter device. Also in some embodiments, the inner plug may be solid and may have a largest cross-sectional diameter of at least 10 mm.

Some of the embodiments including a positioning member may further include a retaining member coupled with a distal end of the positioning member for maintaining the device in intermittent contact with the pyloric valve. In some embodiments, the retaining member self-expands from a first configuration to a second configuration. Such a self-expanding retaining member may expand within the stomach or within the duodenum, in various embodiments. In some embodiments, the retaining member and the obstructing member are in fluid communication through the positioning member. A cross-sectional diameter of the retaining member may be either smaller or larger than a cross-sectional diameter of the support portion in the second configuration, according to various embodiments.

In various embodiments, the retaining member may include any of a number of different features. For example, in one embodiment the retaining member includes at least one hole, ring, loop or other surface feature for attaching a removal device, for removing the obstructing device from the stomach. In one embodiment, the retaining member includes at least one radiopaque marker or material for facilitating visualization of the device. In some embodiments, the retaining member is adapted to deliver at least one therapeutic or diagnostic agent to an intestine distal to the pyloric valve. For example, the retaining member may include a degradable material carrying the therapeutic or diagnostic agent. Alternatively, the retaining member may include one or more housings for releasably containing the therapeutic or diagnostic agent. In other embodiments, the therapeutic or diagnostic agent comprises a coating over at least part of the retaining member. In some embodiments, the retaining member includes an imaging device for imaging an intestine distal to the pyloric valve. The retaining member may also include a chemical measuring device for measuring levels in an intestine of at least one of lipids, sugars, alcohols, drugs, pH levels, pancreatic secretions, biliary secretions and/or other dietary or physiological chemicals.

A retaining member and/or a positioning member having certain dimensions may be advantageous in various embodiments. For example, in one embodiment a retaining member has a cross-sectional diameter of between 0.5 cm and 3.0 cm. In some embodiments, the positioning member has a length of at least 3.0 cm. In some embodiments, the positioning member has a cross-sectional diameter of 2 cm or less. The positioning member may have a general shape adapted to permit the device to intermittently move into and out of contact with the pyloric valve, such as a cylindrical shape or the like. In some embodiments, the positioning member is adapted to self-expand from a first diameter to a larger second diameter within the pyloric valve. In some embodiments, a distal end of the positioning member is weighted.

In a number of embodiments, the device is deliverable into the stomach through an esophagus with the support portion in the first configuration. In some embodiments, for example, a biodegradable covering is disposed over at least the support portion, the covering being adapted to constrain the support portion in the first configuration for delivery into the stomach and to degrade in the stomach to release the support portion from constraint. Whether including such a cover or not, in some embodiments the device is adapted to be swallowed by a patient with the support portion in the first configuration. Such a swallowed device may further include a retaining cord removably coupled with the device and adapted to extend from the device through the patient's esophagus to the patient's mouth. The cord may retain the device in the stomach until it expands from a first configuration to a second configuration, and then may be removed to allow the obstructing device to contact the pylorus. Optionally, the cord may provide for removal of the device if it does not properly deploy in the stomach. In some cases, the cord may be swallowed and may dissolve in the patient's stomach.

In other embodiments, the device may removably couplable with an endoscope, an orogastric tube or any other suitable elongate delivery device for delivery of the device to the stomach through the esophagus. In some embodiments, the device is adapted to be delivered through a lumen of a tube extending from the mouth through the esophagus into the stomach. Optionally, the support portion may be collapsible from the second configuration to the first configuration for removal of the device through the esophagus. Alternatively, the device may comprise one or more biodegradable materials so as to degrade over time and pass through the pyloric valve and the rest of a digestive system. Such biodegradable materials may include but are not limited to cellulose, polyethylene glycol, collagen, polylactic acid and/or other polymers.

The device as a whole may include any of a number of various features in various embodiments. For example, in one embodiment the support portion and/or the tissue engagement portion may include one or more radiopaque materials, dyes and/or markers. One embodiment may further include one or more therapeutic or diagnostic agents releasably coupled with the device for release within the stomach. Optionally, some embodiments include an imaging device coupled with the obstructing device for imaging the stomach, the pyloric valve, and/or the intestine distal to the pyloric valve. Some embodiments may include a chemical measuring device coupled with the obstructing device for measuring levels in the stomach of lipids, sugars, alcohols and/or the like. Some embodiments may include a space occupying member coupled with the obstructing device for occupying space in the stomach to treat obesity. Some embodiments may include one or more electrodes coupled with the device and removably attachable to stomach tissue. In such embodiments, a power source for applying energy to the electrodes, as well as other features, may be housed within the device. Electrodes may be coupled with the device via one or more cords or tethers.

In another aspect of the invention, a device for obstructing a pyloric valve of a stomach comprises an obstructing member adapted to expand in the stomach from a first configuration to a larger second configuration and a positioning member extending from the obstructing member. As described above, the positioning member has a shape adapted to pass at least partially through the pyloric valve to position the obstructing member over the pyloric valve. In some embodiments, the obstructing member self-expands from the first configuration to the second configuration.

In some embodiments, the obstructing member comprises an inner plug and a compliant outer shell. The shell is movable from a first configuration in which it overlaps at least part of the positioning member to a second configuration in which it overlaps at least part of the plug. The plug and a first portion of the shell in the second configuration act as the support portion, and a second portion of the shell in the second configuration acts as the tissue engagement portion. The inner plug and outer shell may have any of the features already described. The device as a whole may also have any of the features described above, in various embodiments. For example, some embodiments further include a retaining member as previously described.

In another aspect of the invention, a system for obstructing a pyloric valve of a stomach includes a pyloric valve obstructing device and a delivery device for delivering the pyloric valve obstructing device to the stomach through the esophagus. The pyloric valve obstructing device includes an expandable support portion adapted to expand in the stomach from a first configuration to a larger second configuration and a compliant tissue engagement portion coupled with the expandable support portion and adapted to engage stomach tissue adjacent the pyloric valve such that the device at least intermittently obstructs the pyloric valve. This obstruction device may optionally be self-expanding and may include any of the other features described above in various embodiments.

In some embodiments, the delivery device comprises an elongate flexible catheter. For example the flexible catheter may comprise an endoscope, an orogastric tube or the like in various embodiments. In some embodiments, the flexible catheter defines a lumen in which the obstructing device is housed during delivery. Such a flexible catheter may optionally further include a coupling mechanism for releasably holding the obstructing device within the lumen during delivery. The delivery device may also be adapted to remove the obstructing device from the stomach through the esophagus, in some embodiments. In an alternative embodiment, the device may be delivery in a collapsed state alongside an endoscope.

In alternative embodiments, the delivery device comprises a biodegradable caplet for containing the obstructing device to allow it to be swallowed by a patient, the biodegradable caplet dissolving within the stomach. In these or other embodiments, the obstructing device may comprise one or more biodegradable materials so as to degrade over time and pass through the pyloric valve and the rest of a digestive system. Such biodegradable materials may include but are not limited to cellulose, polyethylene glycol, collagen, polylactic acid and/or other polymers.

In some embodiments, the system further includes a space occupying member coupled with the obstructing device for occupying space in the stomach to treat obesity.

In another aspect of the present invention, a method for obstructing a pyloric valve of a stomach involves delivering a pyloric valve obstructing device through an esophagus to the stomach and releasing the obstructing device in the stomach to allow it to expand from a first configuration to a larger second configuration. As has been described above, the obstructing device in the second configuration is adapted to at least intermittently contact and obstruct the pyloric valve.

In some embodiments, releasing the obstructing device involves releasing the device from constraint to allow it to self-expand from the first configuration to the second configuration. For example, the obstructing device may be delivered to the stomach via an elongate flexible catheter, tube or scope advanced through an esophagus. In other embodiments, releasing the obstructing device involves allowing a patient to ingest the obstructing device in its first configuration. In some embodiments, for example, the device may be folded or compressed for swallowing, with the device unfolding or expanding upon arrival in the stomach. In another embodiment, delivering the device involves allowing the patient to ingest a biodegradable capsule containing the obstructing device in the first configuration, the biodegradable capsule degrading in the stomach to allow expansion to the second configuration.

Although some methods involve releasing a self-expanding obstructing device, other embodiments may involve actuating the expansion, using one or more delivery devices. For example, in some embodiments the method further involves inflating the obstructing device within the stomach before releasing it. Further details of inflatable obstructing devices and methods for their use can be found in U.S. patent application Ser. No. 10/671,191, of which the present application is a continuation-in-part and which was previously incorporated by reference. In alternative embodiments, the method may further involve moving an expandable shell of the obstructing device from a first position to a second position to expand the obstructing device from its first configuration to its second configuration. For example, in one embodiment the shell may be invert from a position facilitating delivery of the device to a position for obstructing the pyloric valve, using a distal end of a catheter delivery device. In some methods, it may also be possible to adjust buoyancy of the obstructing device before or after releasing it to allow it to migrate naturally within the stomach to contact and obstruct the pyloric valve. Adjusting the buoyancy, for example, might involve introducing a fluid or a gas into one or more chambers of the device.

In many, if not all, embodiments, delivery of an obstructing device is reversible. Reversibility may be achieved by a number of different techniques. In one embodiment, for example, the method for obstructing the pyloric valve further involves collapsing the obstructing device from the second configuration to the first configuration and removing the obstructing device from the stomach through the esophagus. An alternative embodiment involves cutting the obstructing device into multiple pieces and removing the obstructing device from the stomach through the esophagus. In either of these embodiments, the delivering, releasing, collapsing and removing steps may in some cases be achieved via one or more elongate flexible catheters, tubes or scopes advanced through an esophagus. In other embodiments, releasing the obstructing device in the stomach causes the device to begin to degrade. In such embodiments, reversibility is achieved by the device degrading over time and passing harmlessly through the digestive tract.

In some embodiments, the method further includes maintaining the obstructing or occluding device in at least intermittent contact with the pyloric valve by providing the device with a portion that extends at least partially through the pyloric valve. In some embodiments, a first portion of the obstructing or occluding member expands from the first configuration to the second configuration in the stomach, and a second portion of the obstructing or occluding member passes through the pyloric valve into adjacent intestine before expanding from the first configuration to the second larger configuration. Optionally, a bridging portion may extend between the first and second portions, through the pyloric valve, which may expand within the stomach or the pyloric valve. The bridging portion will have a length that allows it to pass through the gastric opening with the first and second obstructing or occluding portions on opposite sides of the opening and is slightly longer than the passage through the opening itself to allow the bridging portion to move longitudinally and intermittently for short distances within the passage and thereby permit the obstructing or occluding members to intermittently obstruct or occlude the passage.

The method may include additional features, such as visualizing at least one radiopaque marker or material of the obstructing device. In some embodiments, multiple radiopaque markers may be used to visualize the orientation of the device. In some case, the entire device is made of a radiopaque material. In another embodiment, the method includes acquiring one or more images of the stomach, the pyloric valve and/or the intestine, using an imaging device coupled with the obstructing device. In some embodiments, the obstructing member has a size in its second configuration that is sufficiently large as to act as a space-occupying device for further treating obesity. In other embodiments, the method may further involve expanding a space-occupying member coupled with the obstructing member within the stomach to further treat obesity.

In yet another aspect of the present invention, a method for obstructing a pyloric valve of a stomach involves passing a pyloric valve obstructing device in a first configuration through a lumen of an elongate catheter device extending through an esophagus to the stomach, advancing the obstructing device at least partially out of a distal end of the catheter device, and expanding the obstructing device from the first configuration to a second larger configuration using the catheter device. In one embodiment, for example, expanding the obstructing device involves inverting a compliant shell covering part of the device from a first, collapsed configuration to a second, expanded configuration, using a distal portion of the catheter device. Optionally, the method may further involve releasing the obstructing device from the catheter device.

These and other aspects and embodiments of the present invention are described in further detail below, with reference to the drawing figures.

BRIEF DESCRIPTION OF THE DRAWINGS

FIGS. 20A to 20C illustrate a method for delivering and deploying the device of FIGS. 19A and 19B.

In FIG. 21A, the device is shown as it is being introduced past the esophageal sphincter. In FIG. 21B, the device is shown fully placed in the stomach.

In FIG. 26A, the device is shown fixed in a relaxed configuration that allows for retention in the stomach. In FIG. 26B, the device is shown in an intermediate configuration, and in FIG. 26C, the device is shown in a deformed configuration for removal or insertion.

DETAILED DESCRIPTION OF THE PREFERRED EMBODIMENTS

Figure 1A:
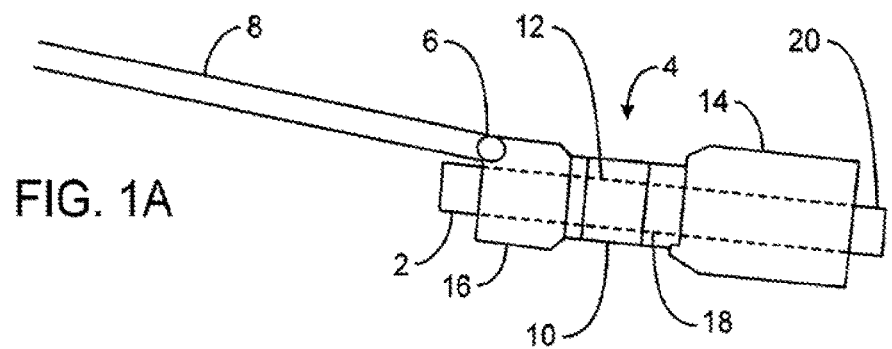
FIGS. 1A to 1C show cross-sectional views of one variation of a pyloric corking device designed to partially and/or intermittently obstruct a gastric opening in an unexpanded, partially unexpanded, and fully expanded configuration, respectively.
Figure 1B:
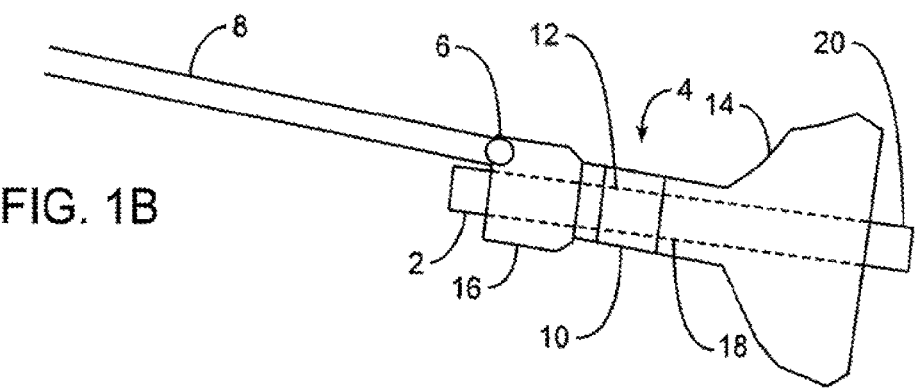
Figure 1C:
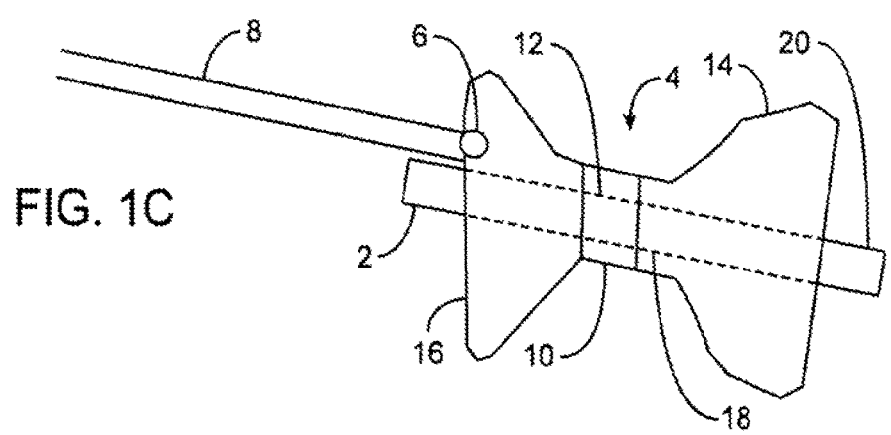

FIGS. 1A to 1C are cross-sectional views showing the expansion, respectively, of one variation of a pyloric corking device which is designed to partially and/or intermittently obstruct a gastric opening, particularly the pyloric valve. In this particular variation, FIG. 1A illustrates the device 4 in an unexpanded or uninflated state and ready for delivery and/or insertion into the pyloric valve. FIG. 11B shows the distal occlusion member 14 in an expanded state. In use, once the device 4 has been placed, e.g., in the pyloric region or beyond, the distal occlusion member 14 (or "retaining member") may be inflated through the influx of any number of biocompatible fluids or gases, e.g., saline, water, air, nitrogen, etc., through the tubing 8 leading to the inflation port 6, which may be self-sealing. Tubing 8 may include any number of delivery tubes such as catheters, endoscopes, etc.

The distal occlusion member 14 may be configured to inflate before the inflation of proximal occlusion member 16 by fabricating the inflatable member of distal occlusion member 14 with a material which is more easily distensible relative to a material of the proximal occlusion member 16. Materials which may be used in fabricating the occlusion members 14, 16 may include any number of materials such as silicone, silicone elastomers, latex, polyurethane, PTFE, FEP, etc. Alternatively, self-expanding materials, such as foam or hydrogels which typically expand upon contact with fluids, may be utilized within the occlusion members 14, 16. If such self-expanding materials are utilized, they may be disposed in the occlusion member 14, 16 and a fluid such as saline, may be infused to expand the materials. Different self-expanding materials may be incorporated in the distal occlusion member 14 than in the proximal occlusion member 16 to obtain differing radial pressures exerted by the expanding materials.

In yet another alternative, an expanding scaffolding or supporting structure of any kind may be utilized within each of the occlusion members 14, 16. Such a scaffold or structure may be made of a shape memory foam, a shape memory alloy or super-elastic alloy, such as Nitinol, or shape memory polymers. The scaffold or structure may be compressed into a delivery configuration and then either allowed to expand into the desired occlusive shape by self-expansion or by supplying an activation energy, e.g., electrical, heat, RF energy, etc. In either case, the distal occlusive member 14 may be positioned distal of the pyloric valve and then inflated or expanded into its larger configuration. It may then be pulled proximally against the pyloric annulus, at which point proximal occlusive member 16 may be inflated or expanded by infusion through port 6, as shown in FIG. 1C. With both occlusion members 14, 16 inflated or expanded, bridging member 10 connecting the two may span the pylorus. Bridging member 10 may be of various diameters, such as 1 mm and less, which does not significantly obstruct the pyloric sphincter, up to 8-10 mm in diameter, which does typically obstruct the pyloric sphincter, or any other suitable diameter.

Bridging member 10 may be designed to have a flexible length sufficient to allow the occlusion members 14, 16 to maintain its position with respect to the pyloric valve yet still enable the members 14, 16 to move. Proximal occlusion member 16 may move from fully obstructing the pyloric valve to moving proximally of the pyloric valve to the extent that distal occlusion member 14 allows member 16 to move. This movement may be elicited by the natural movements of the gastric lumen (stomach) and muscles surrounding the pyloric valve. Thus, when proximal occlusion member 16 is moved proximally, the pyloric valve is only partially obstructed and may allow for the intermittent passage of food between the bridging member 10 and the valve. Because any food within the stomach is retained for longer periods of time, feelings of satiation may be initiated sooner and prolonged so that the patient consumes less food. Moreover, to allow for the relative movement of the occlusion members 14, 16, bridging member 10 may be of a length which is sufficient to allow for its placement through the pyloric valve (or through another gastric opening) such that there is sufficient tolerance for the occlusion members 14, 16 to move proximally and distally relative to the pyloric valve. For instance, in the event that a patient's pyloric valve extends about 2 cm in length, the bridging member 10 is preferably longer than 2 cm, for example, up to 8 cm in length. Moreover, while occlusion members 14, 16 are inflatable or expandable, bridging member 10 itself may be configured to inflate or expand in diameter.

A visible dye or marker, preferably being highly visible, may optionally be infused into one or both of the occlusion members 14, 16 to function as a safety measure. Alternatively, one or both of the occlusion members 14, 16 may optionally be fabricated from a material which is highly visible and visually distinct from tissue so that in the unlikely event of an occlusion member 14, 16 rupturing, the dye or pieces of the occlusion member 14, 16 may become visible once passed from the body. This may indicate to the patient or physician that a rupture of the device has occurred.

Another variation may incorporate slow-releasing drugs infused into the materials covering the device or materials incorporated into the device. These drugs, which may be any number of drugs, may slowly infuse into the patient by drug release into the intestinal tract or through contact with the patient. Alternatively, the devices may incorporate electrical stimulation technologies. For instance, electrical probes may extend from a surface of the device for insertion into the surrounding tissue or electrodes may be formed over a surface of the device instead.

In yet another alternative, the occlusion members 14, 16 may be covered by an erodable or biodegradable covering over one or both members 14, 16. Such a covering may be configured to constrain one or both members 14, 16 and once the device has been ingested or placed within the gastric lumen, contact with the surrounding fluids may naturally erode the covering thus allowing the covered occlusion member to expand or inflate. In another variation, proximal and distal occlusion members may each be covered by different materials each configured to erode at differing rates or in different environments, as described in further detail below.

In the variation shown in FIGS. 1A to 1C, the device 4 may include an optional lumen 18 defined through the device 4. Optional lumen 18 may allow for the passage of fluids and food through the device 4 entering the lumen 18 through entry port 2 and exiting through the exit port 20. The lumen 18 may be designed to allow for the passage of a reduced volume of food through the device 4, in which case the device 4 shown may be configured with a relatively shortened bridging member 10 to inhibit the relative movement of the device 4 relative to the pylorus. With this variation, the lumen 18 has been configured so that it may be capable of actively pumping or metering the contents of the gastric lumen 74 into the intestine 76 through the device 4. In such a case, the need for the device 4 to be able to move to un-occlude the pyloric valve is removed. As shown in the figures, an optional pump or active metering valve 12 may be incorporated into the device 4. Pump or valve 12 may be configured to simply open and allow for the passage of the stomach contents through lumen 18 and valve 12 upon sensing the presence of foreign objects, such as food, in the stomach or upon sensing a predetermined pressure from the contents. Other sensing parameters may include temperature and pH levels. Alternatively, the pump or valve 12 may be configured to actively pump the stomach contents through the lumen 18 via a pumping mechanism automatically activated by pump or valve 12 or externally activated by the patient or physician through wireless communication. In the case where the device is configured with a valve 12, the valve may be configured as a unidirectional valve to allow the flow of fluids and food only from the stomach to the intestinal tract.

Figure 2A:
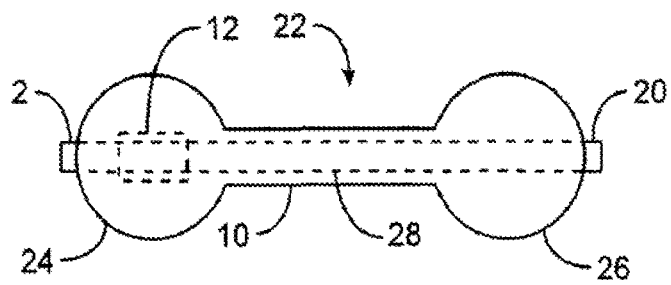
FIGS. 2A to 2D show side views of variations of the device utilizing occlusion members of different shapes.

The device 4 could have any shape provided that the shape and/or total volume of the proximal occlusion member 16 is sufficient to prevent its passage through the pyloric valve and into the intestines. FIGS. 2A to 2D show side views of different shape variations which are possible for use as occlusion members. For instance, FIG. 2A shows a side view of a device variation 22 in which proximal and distal occlusion members 24, 26 have a cross-sectional shape along a longitudinal axis defined by the device 22 in the form of circles, to form spherical occlusion members. Although proximal and distal occlusion members 24, 26 are illustrated having equally sized diameters, the diameters may be varied depending upon the desired shape and device configuration. For instance, proximal occlusion member 24 may be configured to have a diameter larger than distal occlusion member 26. Alternatively, a device having the opposite configuration may also be utilized, although this may be less preferable. Lumen 28 and pump or valve 12 may be optionally included, again depending upon the desired device configuration.

Figure 2B:
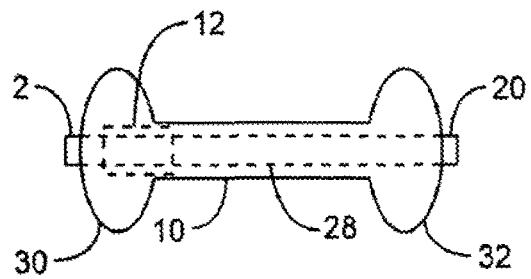
Figure 2C:
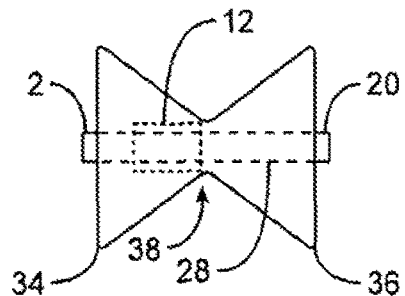
Figure 2D:
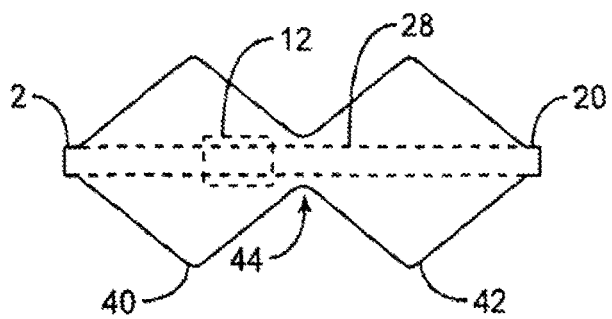

FIG. 2B shows another device variation in which proximal and distal occlusion members 30, 32 may have a cross-sectional shape along a longitudinal axis defined by the device in the form of ellipses, to form ellipsoids. The major axes of the elliptically-shaped occlusion members 30, 32 are preferably oriented perpendicularly relative to the longitudinal axis of the device in this variation, although various angles may be formed as well. FIG. 2C shows the variation in which proximal and distal occlusion members 34, 36 may be formed as triangles, to form conically-shaped occlusion members. In this variation, bridging member 38 may be minimal in length and may simply be formed by the intersection of the occlusion members 34, 38 to form a waist region. FIG. 2D shows yet another variation in which proximal and distal occlusion members 40, 42 may be formed as diamond shapes, to form a variation of conically-shaped occlusion members. This variation may also form a waist region 44.

Although these variations show specific shapes, these are merely intended to be illustrative of the various types of shapes which may be utilized and is not intended to be limiting. For instance, any shape, such as rectangles, squares, etc., which may function to occlude a gastric opening and prevent the device from falling therethrough may be utilized and are within the scope of this disclosure. Moreover, various combinations of the different shapes as occlusion members on a single device may also be utilized, such as a device having a distal occlusion member in the shape of a sphere and a proximal occlusion member in the shape of a cone.

Figure 3A:
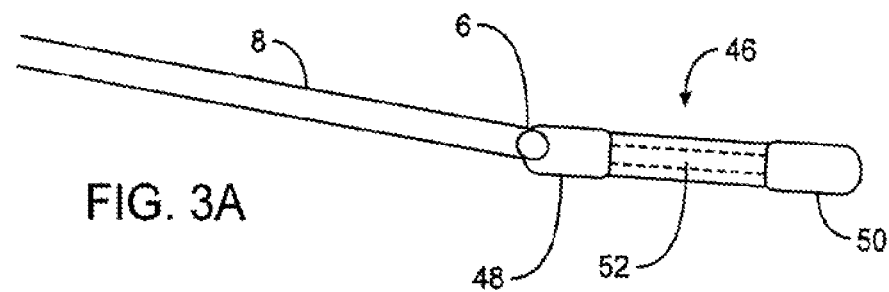
FIGS. 3A to 3C show cross-sectional views of another variation of the pyloric corking device.
Figure 3B:
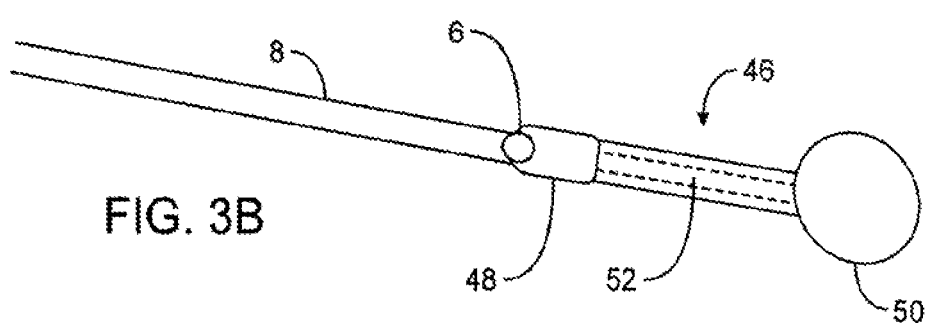
Figure 3C:
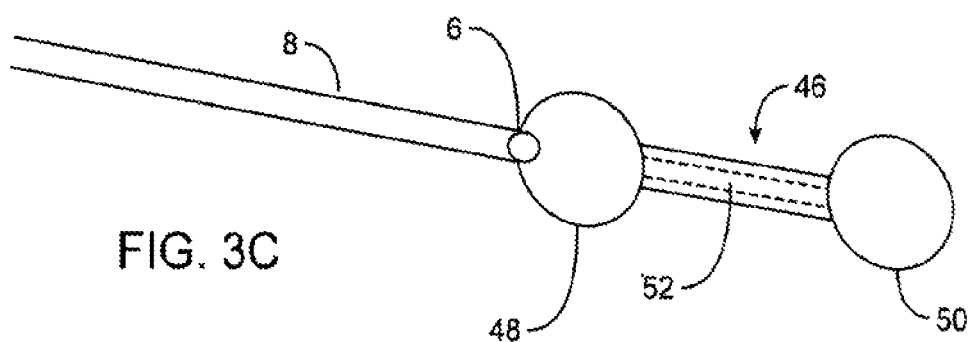

FIGS. 3A to 3C show cross-sectional views of another variation of a pyloric corking device which is also designed to intermittently obstruct a gastric opening. Similar to the device shown in FIGS. 1A to 1C, this particular variation omits the use of a lumen defined through the entire device 46. This device 46 may also incorporate any of the features described above for expanding the occlusion members. For instance, foam of varying expansion pressures may be utilized to ensure that expansion occurs in the distal occlusion member 50 prior to expansion in the proximal occlusion member 48 upon the injection of a fluid, e.g., saline or water, into the device 46. The device 46 is configured so that the influx of fluids from the infusion tubing 8 through the entry port 6 is channeled through the lumen 52 of the central portion from the proximal occlusion member 48 to the distal occlusion member 50. The device 46 may also be placed in the same manner as a device as in FIGS. 1A to 1C, as described in further detail below. This variation may also incorporate an inflation port 6, which may be metallic, so that removal of the device 46, if necessary, can be accomplished through the simple placement of a magnetically tipped suction catheter. The catheter, when appropriately placed, may cause the device to deflate by applying a suction force to facilitate the easy removal of the device 46 from the pyloric valve. With a metallic ring placed around the inflation port of the device, the magnetically tipped suction catheter can be advanced into the patient, or placed using a nasogastric tube. A sensor can then indicate that the magnet has engaged the metallic ring, a vacuum can be activated, and the entire device deflated through rupture of a pressure-sensitive barrier or through the simple application of vacuum forces. The device 46 can thus be removed through any endoscopic or percutaneous approach, e.g., an oro- or nano-gastric approach. While this variation may have a lumen 52 connecting the proximal 48 and distal 50 occlusion members, this lumen 52 may be closed to gastric space and instead be used to communicate an inflation fluid to inflate the occlusion members 48, 50. The occlusion members of the device 46 may have any shape as described above, for instance in FIGS. 1A to 2D.

Figure 4A:
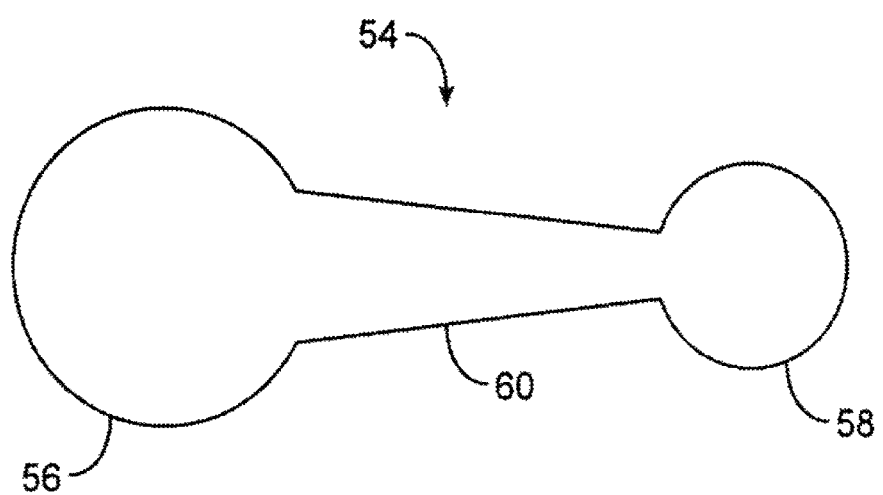
FIG. 4A shows a side view of yet another variation of the device having a tapered bridging member.

Yet another variation of the device is shown in FIG. 4A. In this variation, the device 54 may have a bridging member 60 which is tapered. The bridging member 60 may be tapered to become wider along its length from the distal occlusion member 58 to the proximal occlusion member 56. The tapered bridging member 60 may be utilized to facilitate movement of the device 54 to un-occlude the pyloric valve. As the pyloric valve contracts about the bridging member 60, the taper may aid in moving the device proximally. The angle of the taper may be varied, depending upon the desired results, as may the size and shapes of the occluding members 56, 58.

Figure 4B:
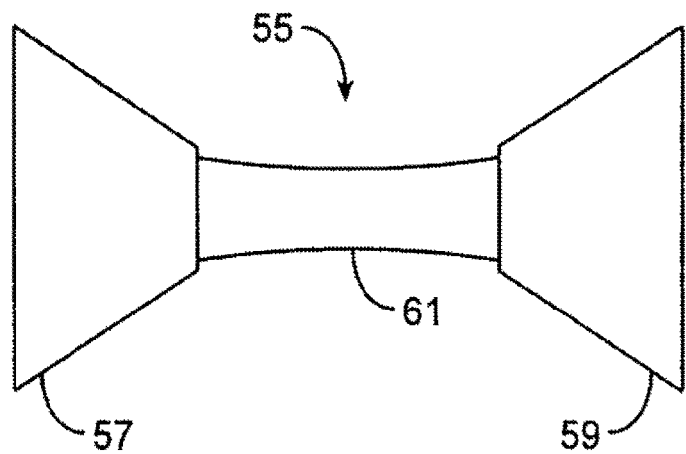
FIG. 4B shows a side view of yet another variation of the device having conical occlusion members held at a distance from one another.

FIG. 4B shows another variation similar to that shown above. In this variation, the device 55 may have occlusion members 57, 59 having conically-shaped members which are connected via a bridging member 61. This bridging member 61 may have a length which holds occlusion members 57, 59 at a distance from one another sufficient to enable the device 55 to move relative to the pyloric valve. The device 55 may inflate or expand the occlusion members 57, 59 using any of the methods disclosed herein and the device 55 may also optionally incorporate a central lumen and a passive or active valve or pumping mechanism, if desired.

Figure 5A:
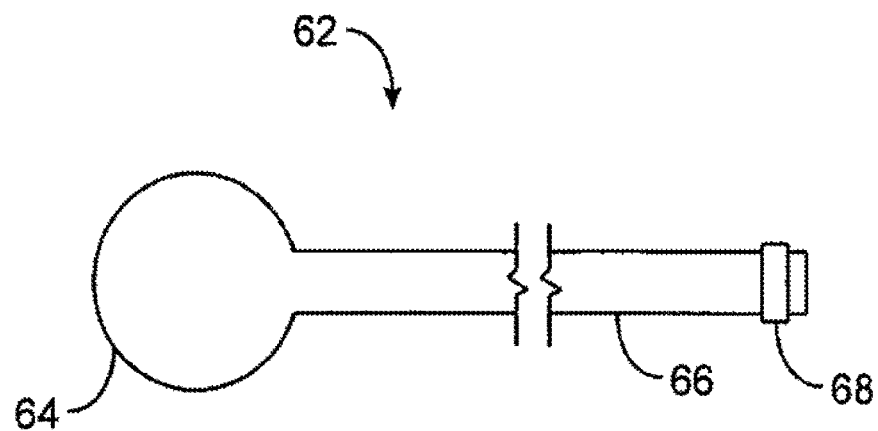
FIGS. 5A and 5B show side views of yet another variation of the device having a single occlusion member and alternative anchor members.
Figure 5B:
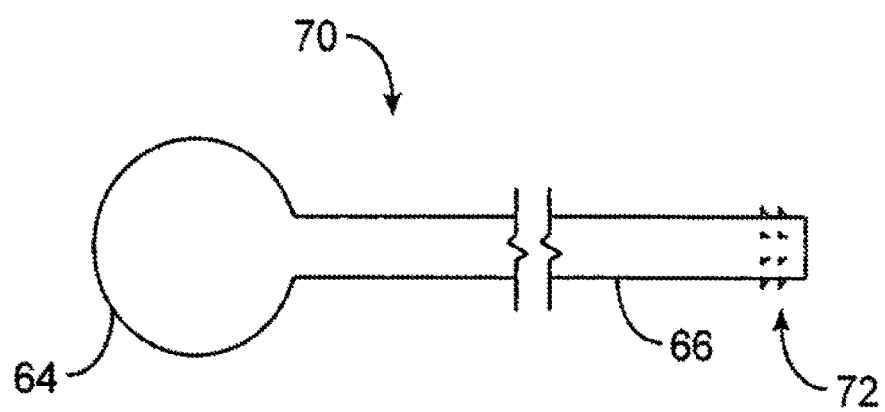

In another embodiment, the distal occlusion member may be omitted entirely. FIG. 5A, for instance, shows a side view of an alternative variation 62 in which the bridging member 66 (or "positioning member") may extend at some length, e.g., 5 cm or greater, from a proximal occlusion member 64. The bridging member 66 may be placed within the intestinal tract. e.g., the duodenum, while held in place by the proximal occlusion member 64 abutting the pyloric valve. The positioning of the proximal occlusion member 64 relative to the pyloric valve may be maintained by the frictional forces generated by the bridging member 66 rubbing against the walls the intestinal tract. The occlusion member 64 may function in the same manner as described above in intermittently un-occluding the pyloric valve during stomach contractions and movement, but may be held in place by the length of the bridging member 66. Although the distal end of the bridging member 68 may be free-floating in the intestinal tract, it may optionally be weighted by a weight 68 or by a number of hooks or barbs 72 for attachment to the intestinal walls, as shown in the device 70 of FIG. 5B.

It is furthermore within the scope of this disclosure that certain features between the different device variations described herein may be incorporated into various combinations. For instance, a device having a proximal occlusion member having a spherical shape and a distal occlusion member having a conical shape may be utilized. As a further example, this device may also incorporate various methods to inflate or expand the distal occlusion member in a different manner as the proximal occlusion member. Moreover, this device may also have a biodegradable covering over only one occlusion member and may also incorporate the valve and/or pump integrated within the device and may also optionally include a lumen defined throughout the length of the device. These examples are merely intended to be illustrative of the various combinations which may be employed by combining various aspects from different variations described herein and are intended to be within the scope of this invention.

Figure 6A:
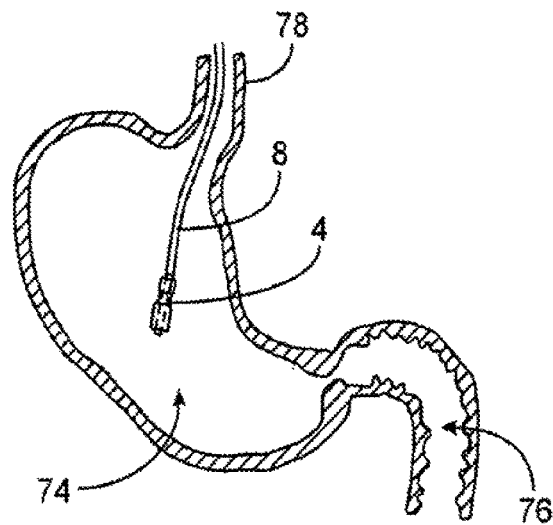
FIGS. 6A to 6C show cross-sectional views of the stomach and one variation for nasogastric (or endoscopic) placement of a non-ingestible variation of the device.
Figure 6B:
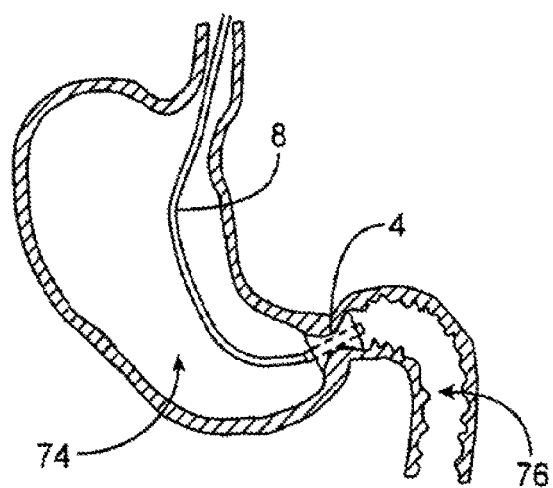
Figure 6C:
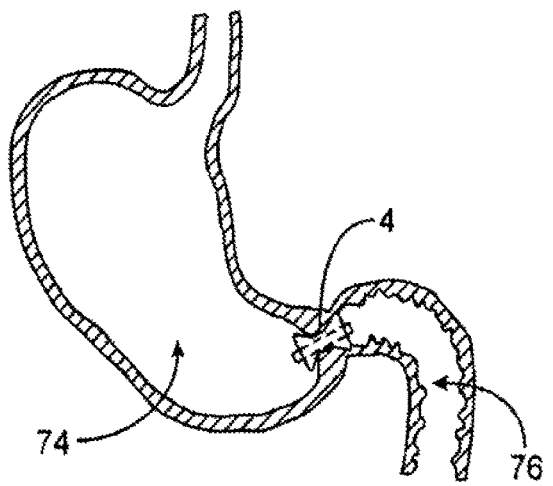

FIGS. 6A to 6C show cross-sectional views of the stomach and one variation for nasogastric (or endoscopic) placement of a non-ingestible, active variation of the device 4. As the device 4 is delivered through the esophagus 78, it may be in a compressed, un-inflated, or un-expanded configuration, as shown in FIG. 6A, while being positioned via the optional tubing 8. Once the device 4 has been positioned to span the pylorus with the occlusion members in the stomach 74 and duodenum 76, respectively, the device 4 may be inflated or expanded using any of the methods described above, as shown in FIG. 6B. The tubing 8 may then be detached and the device 4 left in place, as shown in FIG. 6C.

Figure 7A:
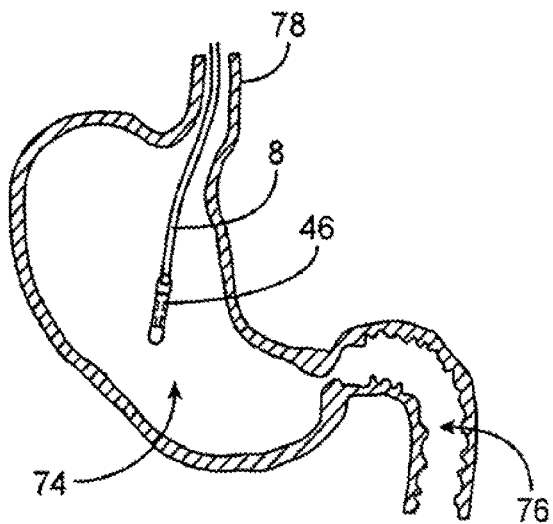
FIGS. 7A to 7C show cross-sectional views of the stomach and another variation for nasogastric (or endoscopic) placement of a non-ingestible variation of the device.
Figure 7B:
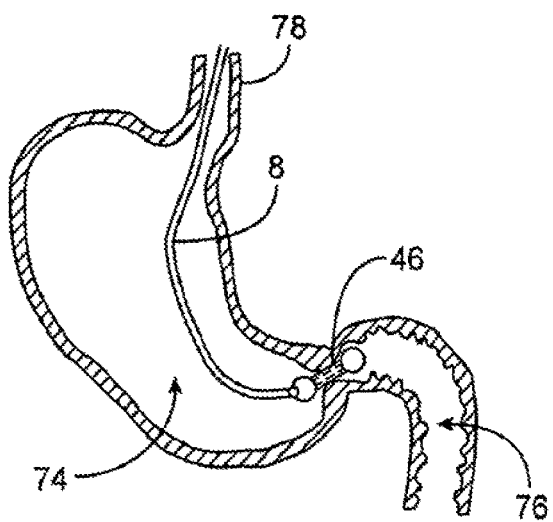
Figure 7C:
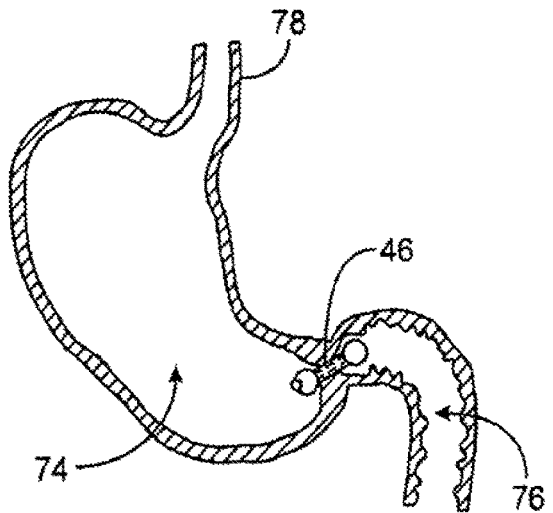

FIGS. 7A to 7C show cross-sectional views of the stomach and another variation for nasogastric (or endoscopic) placement of a non-ingestible, passive variation of the device 46. As above, the device 46 may be advanced through the esophagus 78 while in a compressed, un-inflated, or un-expanded configuration, as shown in FIG. 7A. As shown in FIG. 7B, once the device 46 has been placed spanning the pylorus with the occlusion members in the stomach 74 and duodenum 76, respectively, the device may be inflated or expanded and the tubing 8 may be detached and the device 46 left in place, as shown in FIG. 7C.

Figure 8A:
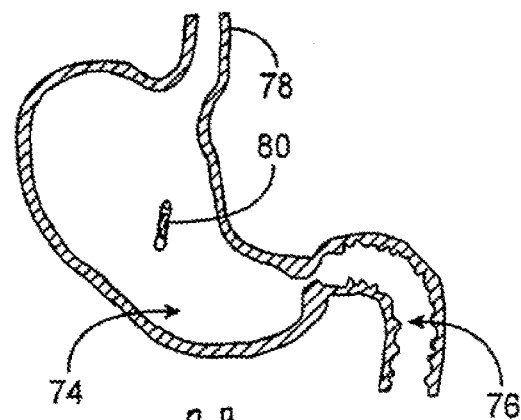
FIGS. 8A to 8D show cross-sectional views of the stomach and yet another variation for placement of a variation of the device through ingestion.
Figure 8B:
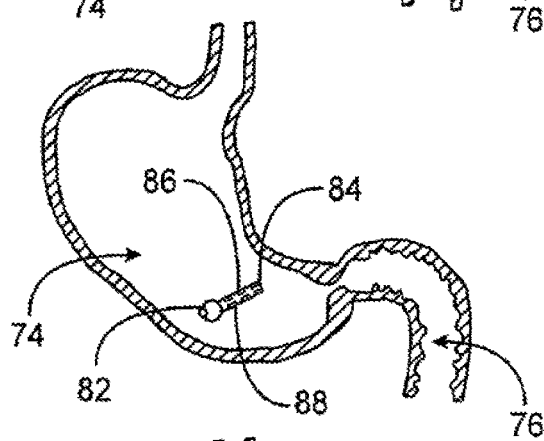
Figure 8C:
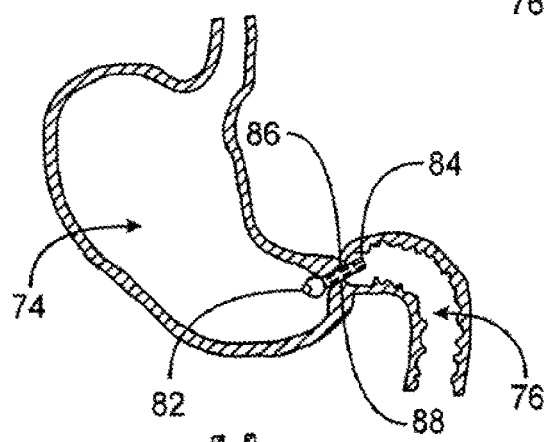
Figure 8D:
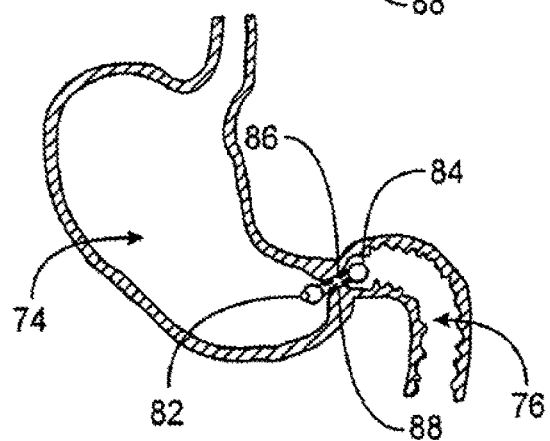

FIGS. 8A to 8D show cross-sectional views of the stomach and yet another variation for placement of a passive (or "self-expanding") embodiment of the device 80. As shown in FIG. 8A, the device 80 may be simply ingested. As it enters the stomach 74, gastric fluids may erode an acid sensitive coating over the inflation port of the proximal occlusion member 82. Once the coating has degraded, the proximal occlusion member 82 may be configured to expand or inflate, as shown in FIG. 8B. Once the expansion or inflation has occurred, the device 80 will remain in the stomach 74 and eventually the distal occlusion member 84 may pass into the duodenum 76 while still in its un-expanded or un-inflated state due to the natural contractions of the stomach, as shown in FIG. 8C. Once the distal occlusion member 84 has passed into the duodenum 76, an alkaline sensitive coating over the distal occlusion member 84 may be eroded and expansion or inflation of the distal occlusion member 84 will occur with the device spanning the pyloric valve, as shown in FIG. 8D. The covering over the distal occlusion member 84 may be configured to erode only once it has contacted the acidic environment specific to the duodenum 76, where the pH level is approximately 6. In order to facilitate removal, the two occlusion members 82, 84 may be connected by a central, hollow lumen 86, as described above, with a barrier 88 designed to rupture upon the application of a predetermined pressure level. Thus, with application of a vacuum having the appropriate pressure level, the barrier 88 may be configured to rupture and the entire device 80 may be deflated.

Figure 9A:
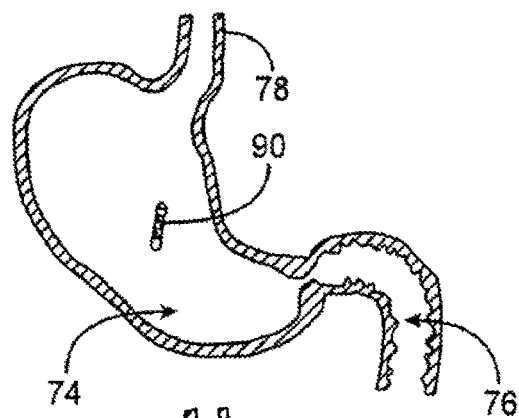
FIGS. 9A to 9D show cross-sectional views of the stomach and yet another variation for placement of another variation of the device through ingestion.
Figure 9B:
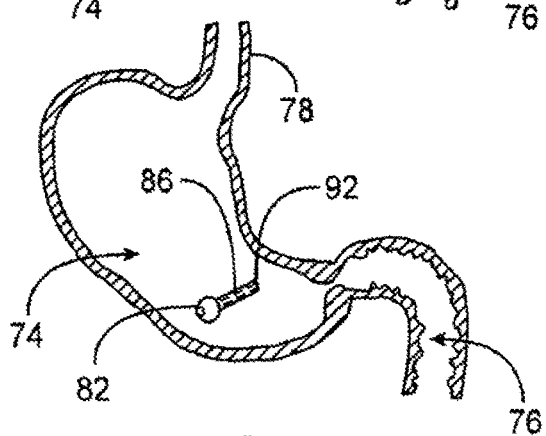
Figure 9C:
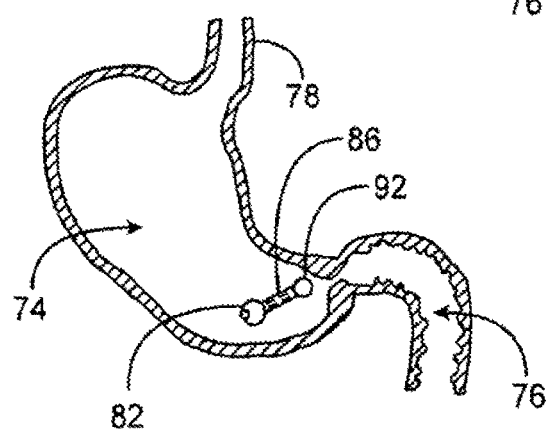
Figure 9D:
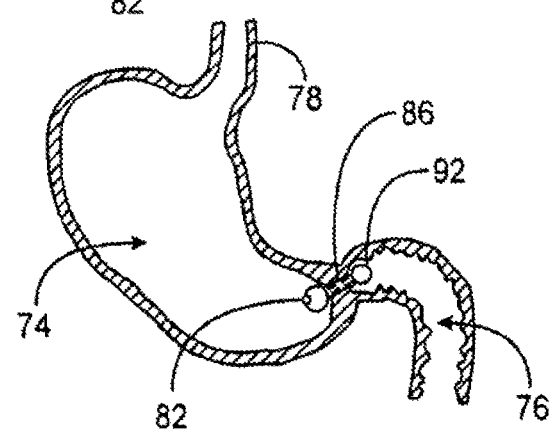

FIGS. 9A to 9D show cross-sectional views of the stomach and yet another variation for placement of a passive variation of the device 90 through ingestion. In this alternative variation, the device 90 can be ingested orally. As the device 90 enters the stomach 74, shown in FIG. 9A, both the proximal and distal occlusion members 82, 92, respectively, may be configured to inflate upon erosion of acid-sensitive coatings over the inflation port or device 90, as shown in FIGS. 9B and 9C. Once inflation or expansion has been accomplished, the distal occlusion member 92 will eventually be passed due to its smaller size (approximately the diameter of the dilated pyloric valve 5-15 mm) while the proximal occlusion member 82 will remain in the stomach 74 due to its larger size, e.g., 15 mm or greater in diameter and up to 60 mm in diameter due to physiologic limitations in the pyloric region of the stomach, as shown in FIG. 9D. Thus, one occlusion member 92 may be designed to be small enough to be passed through the pyloric valve while the proximal occlusion member 82 may be designed to be retained in the stomach 74 with both occlusion members 82, 92 inflating in the stomach 74. One of the occlusion members can have an inflation port covered with an acid-sensitive coating while the other is acid-resistant bur erodes at the pH found in the intestine (approximately 6.0). Thus, once the device is ingested, one of the occlusion members will expand retaining the device in the gastric space after which gastric motility will eventually move the remaining uninflated occlusion member into the intestine. Once the second occlusion member contacts the intestinal tract, the inflation port may be eroded by the intestinal milieu and the second portion may slowly inflate leaving the device spanning the pyloric valve.

A number of different alternatives and variations may be employed in self-expanding or "passive" pyloric valve obstructing devices and methods such as those just described. In some embodiments, a device may be folded, compressed or otherwise formed into a smaller configuration for swallowing by a patient, without using a biodegradable coating. Upon passing through the esophagus into the stomach, the folded device may unfold due to one or more shape-memory Nitinol support rings or other self-expanding support members. In any swallowing embodiment, a device may also include a tether that extends from the device, back through the esophagus to the patient's mouth. Such a tether may be used for retaining the obstructing device in the stomach until it expands, retrieving the obstructing device if it does not deploy as desired in the patient's stomach and/or the like. In some embodiments, the tether may be swallowed to dissolve in the stomach. In other embodiments, a swallowed device may contact the pyloric valve but not include a bridging member for spanning the valve. Other variations are contemplated within the scope of the invention, according to various embodiments.

Figure 10A:
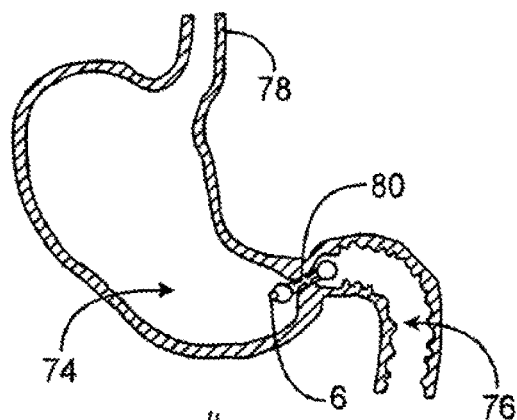
FIGS. 10A to 10D show cross-sectional views of the stomach and one variation for removal of the device.
Figure 10B:
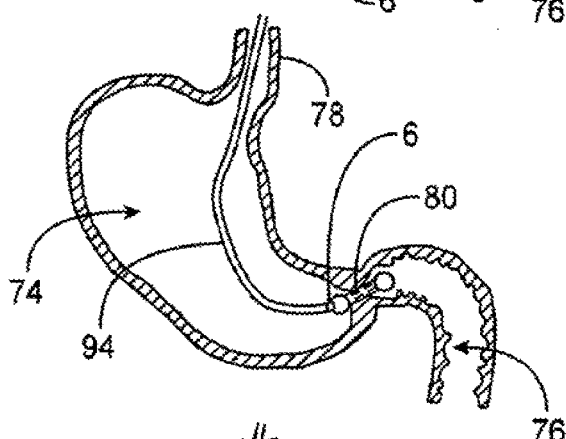
Figure 10C:
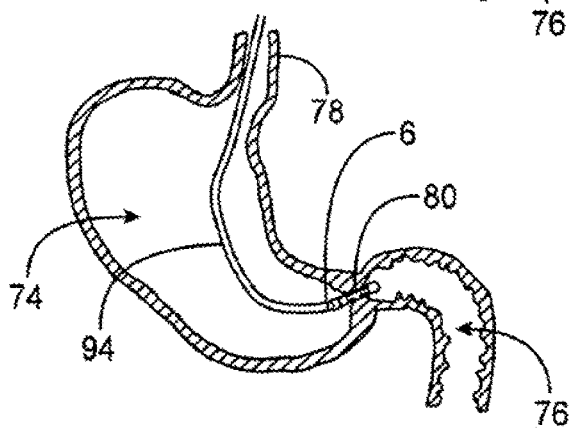
Figure 10D:
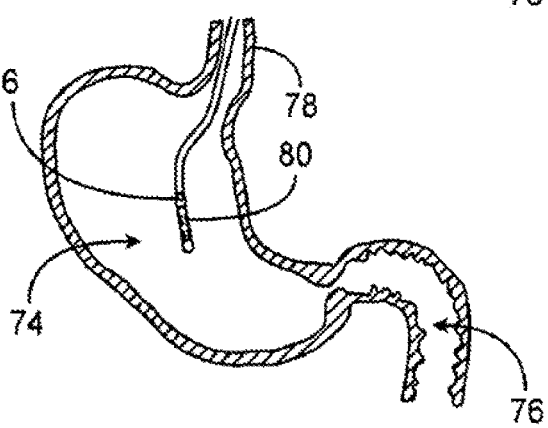

FIGS. 10A to 10D show cross-sectional views of the stomach 74 showing one variation for removal of the device 80 (passive variation illustrated). The device 80 is shown in FIG. 10A between the stomach 74 and the duodenum 76. As seen in FIG. 10B, a magnetic tipped suction catheter or endoscope 94 is introduced and the device 80 may be deflated and removed, as shown in FIGS. 10C and 10D. In contacting the inflation port 6 with the catheter 94, the tip may be configured with an electrical contact as an aid in determining whether the catheter 94 has properly contacted the inflation port 6. Alternatively, the device 80 may be removed through endoscopy or it may be designed to degrade over time and eventually be passed through the intestines.

In other embodiments, an obstruction device may be removed by deflating or collapsing the device and removing it through a lumen of a catheter device. In one embodiment, the device may be cut into small pieces and removed through a catheter lumen in yet another embodiment, the device may dissolve over time and pass harmlessly through the pyloric valve and the digestive system. Any number of suitable alternatives for removal or passage of the device are possible in various embodiments.

Figure 11A:
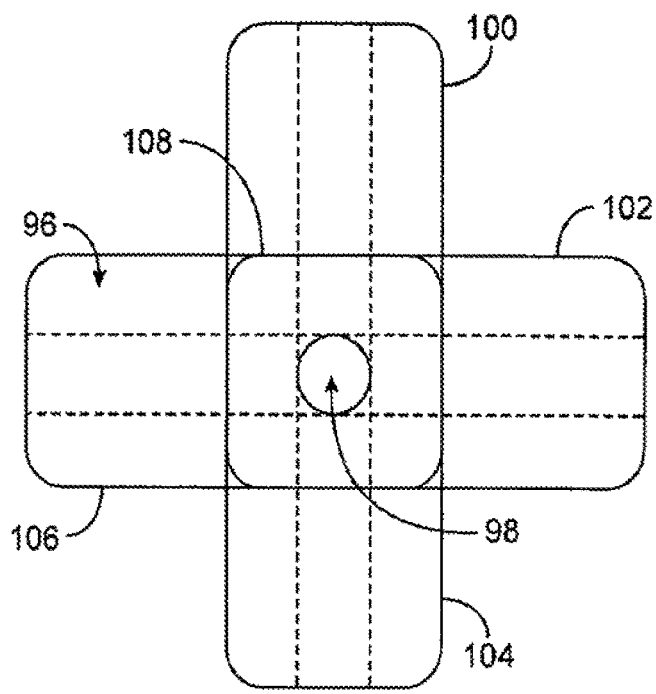
FIGS. 11A and 11B show top and perspective views, respectively, of an alternative variation of the device incorporating multiple prongs designed to intermittently obstruct the pyloric valve.
Figure 11B:
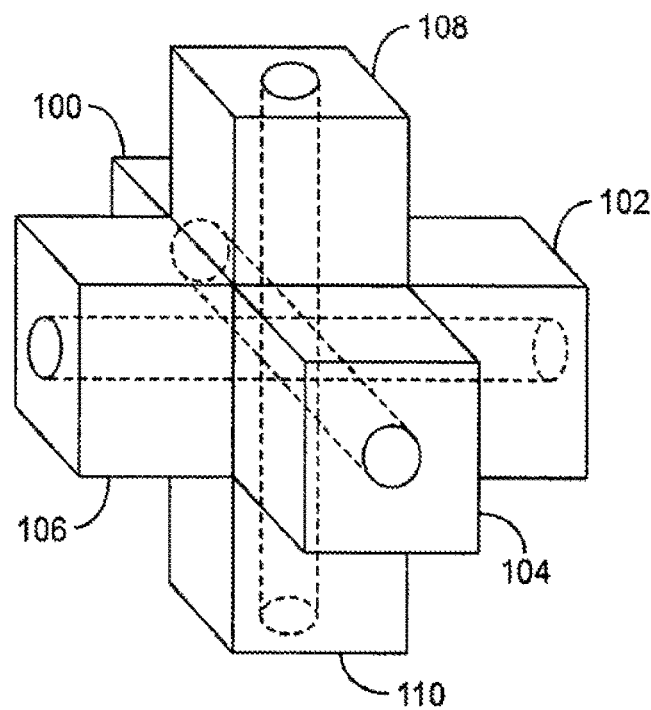

FIGS. 11A and 11B show top and perspective views, respectively, of an alternative variation for the device which may reside solely in the stomach. This particular variation may incorporate multiple prongs 100, 102, 104, 106, 108, 110 designed to intermittently cork the pylorus. In this variation, an expansile material 96 may be appropriately shaped in order to promote occlusion of the pylorus. The device may be ejected from the pylorus due to contractions, but may be re-inserted through one of the various prongs. As a further measure, the device may define multiple apertures 98 through each set of prongs to prevent complete obstruction of the pyloric valve.

Figure 12A:
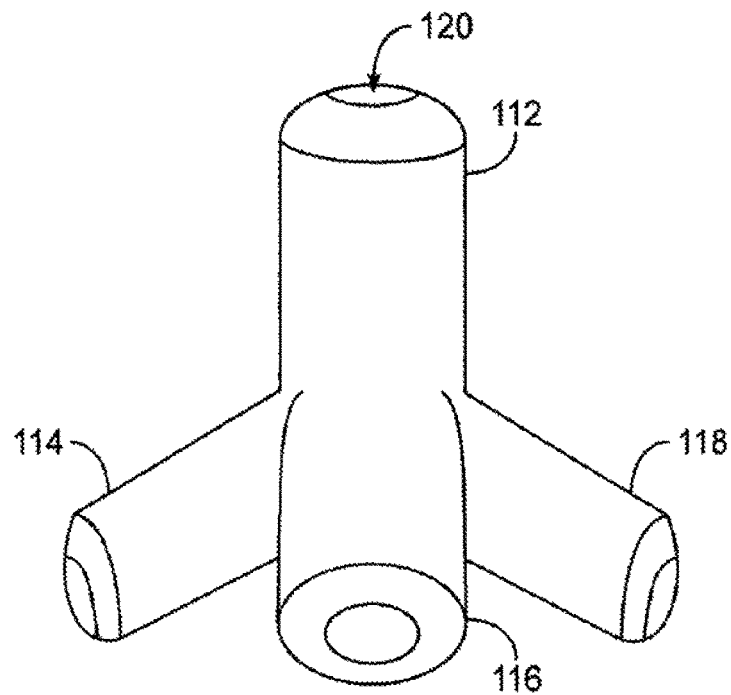
FIGS. 12A and 12B show side and top views, respectively, of another variation of the device incorporating multiple prongs designed to intermittently obstruct the pyloric valve.
Figure 12B:
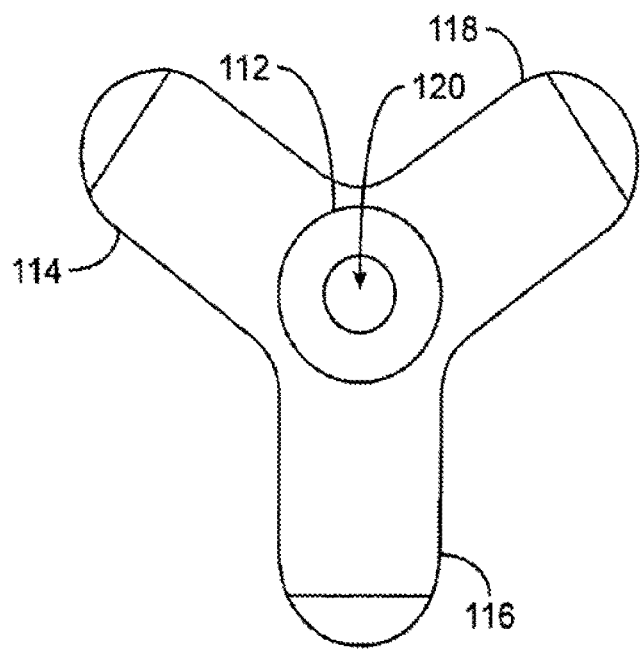
Figure 13A:
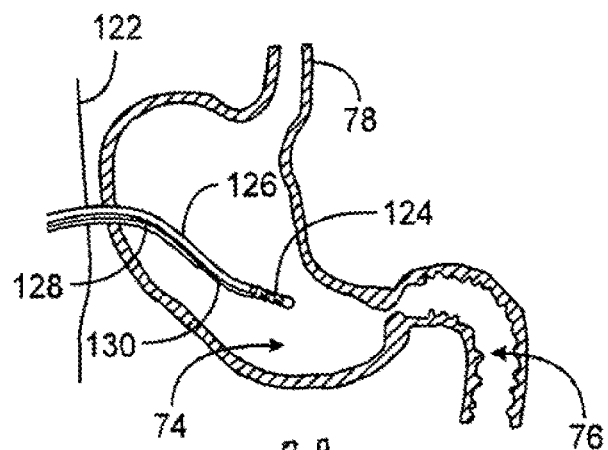
FIGS. 13A to 13D show cross-sectional views of an alternative use of the device for preventing gastroduodenal reflux during tube feeding.
Figure 13B:
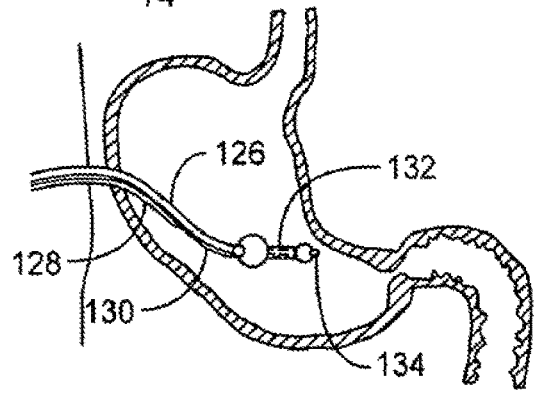
Figure 13C:
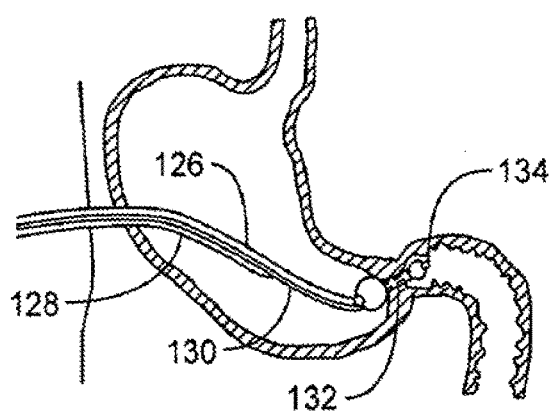
Figure 13D:
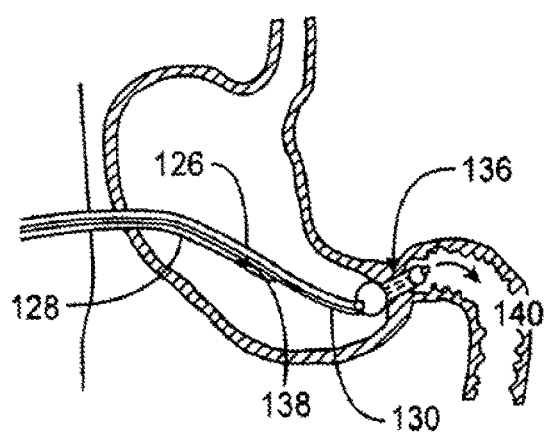

FIGS. 12A and 12B show side and top views, respectively, of another variation of A device as in FIGS. 11A and 11B. In this variation, a fewer number of multiple prongs 112, 114, 116, 118 may be utilized and each prong may also define an aperture 120 therethrough. However, as shown in this variation, each of the prongs may be flexible and tapered or rounded to prevent damage to the surrounding tissue.

FIGS. 13A to 13D show cross-sectional views of an alternative use of the devices described herein. In this variation, the device may be utilized in the prevention of gastroduodenal reflux during tube feeding. As shown, the device 124 is similar to variations described above; however, in this variation, a lumen 132 defined through the device 124 for tube feed delivery may define an outlet 134 designed to be positioned in the duodenum 76. The proximal portion of the device 124 may also be attached to a feeding tube 126 and an inflation tubing 130. Feeding tube 126 may be used to deliver tube feeds through the lumen 132 directly to the duodenum 140 while the inflation tubing 130 may be used to inflate an inflatable pyloric spanner or bridging member 136 during tube feeding to prevent reflux of delivered material 140. The device 124 can also incorporate a third tube 128 which may provide for aspiration of the gastric contents 138 to prevent reflux of the delivered material into the lungs and to decompress the stomach 74. The proximal portion of the occlusive member can either maintain its inflated or expanded state or it can be decompressed at times to relieve pressure on the pyloric valve. In this variation, a percutaneous approach is shown, but a nasogastric approach or another approach is possible.

Figure 14A:
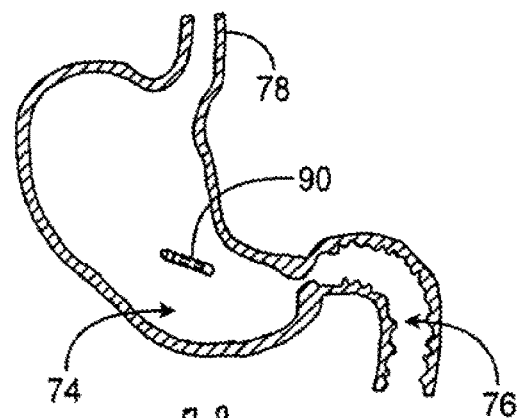
FIGS. 14A to 14D show cross-sectional views of an alternative use of the device in combination with one or several gastric fillers.
Figure 14B:
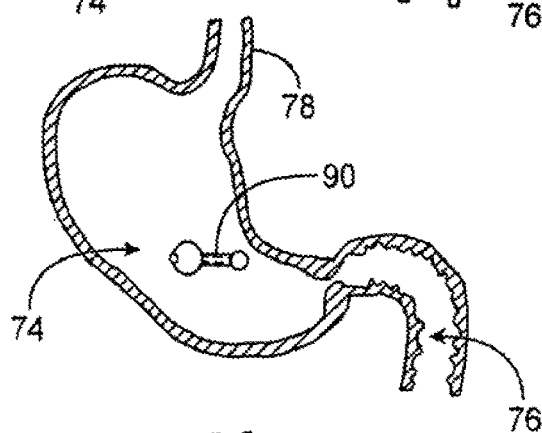
Figure 14C:
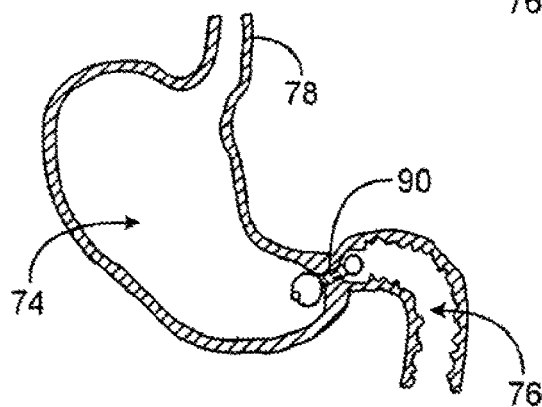
Figure 14D:
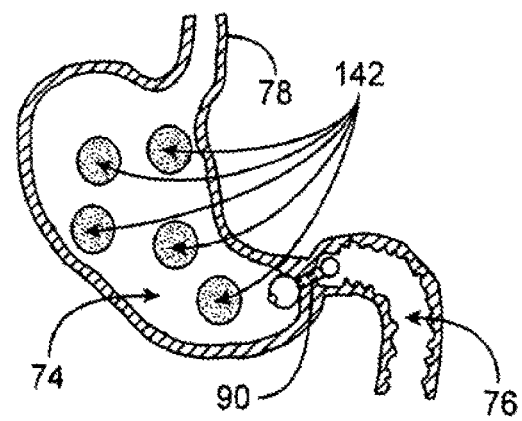

FIGS. 14A to 14D show cross-sectional views of yet another alternative use of devices of the present invention. As shown in FIGS. 14A to 14C, a device 90 may be placed to occlude the pyloric valve. In this case, the device 90 is shown as having been ingested, although placement of the device 90 may be affected via any of the methods described above. As shown in FIG. 14D, the addition of one or several gastric fillers 142, e.g., inflatable gastric balloons, expandable scaffolding, or any other number of space-occupying devices generally known in the art, may be utilized. In this variation, the device 90 may be placed and then the gastric fillers 142 may be introduced. The device 90 may be utilized to ensure that the gastric fillers 142 are not passed through the pyloric valve until they are sufficiently small, thereby allowing for non-degradable substances to be utilized without the concomitant risk of small bowel obstruction.

Figure 15A:
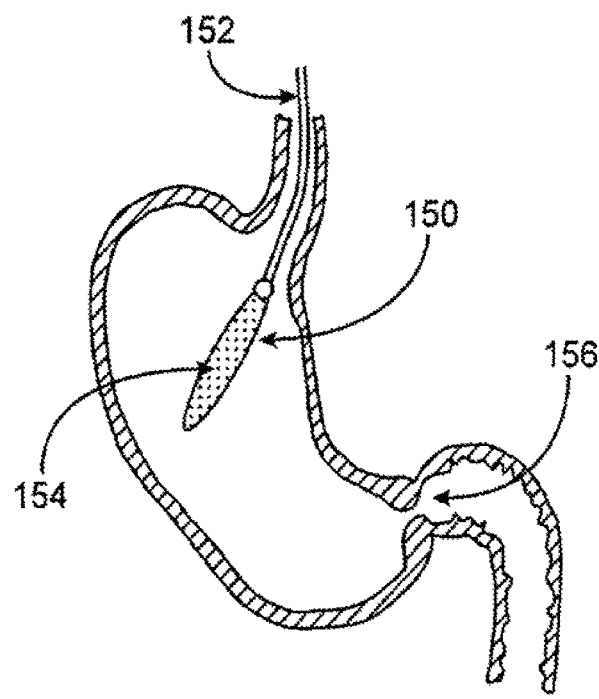
FIGS. 15A to 15D show cross-sectional views of a device designed to partially displace intragastric volume and intermittently obstruct a gastric opening, according to one embodiment of the present invention.
Figure 15B:
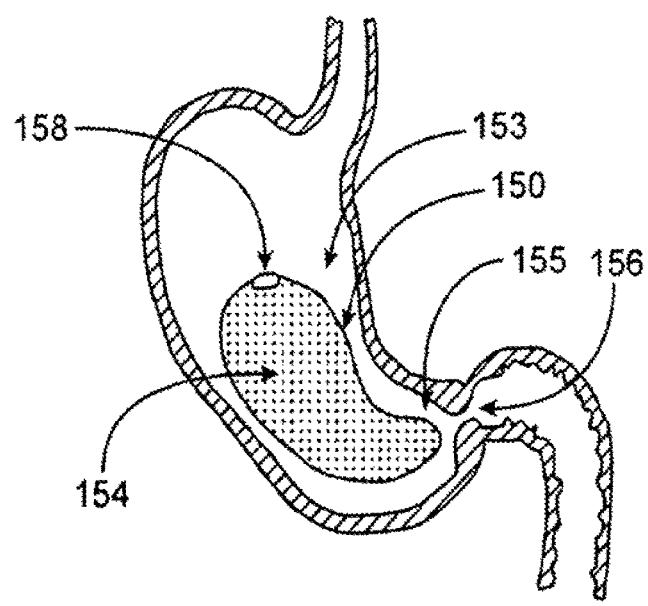

FIGS. 15A to 15D are cross-sectional views demonstrating the use of another embodiment of a device 150 for intermittently obstructing a pyloric valve 156, and in this embodiment for partially filling the gastric space. FIG. 15A illustrates the device 150 in an unexpanded or uninflated state and ready for delivery and/or insertion into the stomach via a catheter device 152, such as an endoscope, tubing or the like. The device, in this embodiment, includes an expandable foam 154, which is expanded when the device 150 is within the stomach, as shown in FIG. 15B. Any suitable nontoxic liquids or gases may be introduced through an inflation port 158, for expanding the device 150 and/or the foam 154.

Any suitable materials may be used to form the device 150. In one embodiment, for example, the device 150 may comprise an expandable balloon fabricated from silicone, silicone elastomers, latex, polyurethane, PTFE, FEP, and/or the like. The internalinflatable lumen of the balloon can be filled with an expansile cohesive material such as a dehydrated and crosslinked PEG, a dehydrated hydrogel, or other swellable mass, or buttressed with a shape memory material such as a shape memory foam, shape memory metals (such as Nitinol), or shape memory polymers. The buttressing materials can be placed anywhere on the device, including inside the flexible balloon material. Alternatively, the wall of the balloon itself can be composed of a shape memory material, obviating the need for any filling or buttressing. If self-expanding materials are utilized, they may be disposed inside the balloon, and the balloon may be infused with a fluid such as saline to expand the materials.

As shown in FIG. 15lB, the device 150 in one embodiment includes a proximal portion 153 and a distal portion 155. In some embodiments, the proximal portion 153 has a supportive or structural function, for assuring that the device 150 has a large enough cross sectional diameter to prevent passage of the device 150 through the pyloric valve. Typically, the distal portion 155 functions to contact the pyloric valve 156 and/or tissue adjacent the pyloric valve 156, to intermittently and/or partially block the valve 156. In some embodiments, the distal portion 155 is made of compliant material, so that when it contacts stomach tissue in, around or adjacent the pyloric valve 156, it does not harm the tissue. In some embodiments the proximal portion 153 and distal portion 155 are made of the same material, with the proximal portion 153 having a greater amount of material, greater wall thickness or the like, relative to the distal portion 155.

Generally, the device 150 may have any of a number of suitable shapes, such as an irregular oblong shape as shown, an elongated spherical shape, a cone, a diamond or the like. In some embodiments, the shape is selected such that the device 150 naturally migrates toward the pyloric valve 156, with the distal portion 155 aligned to contact the valve 156. In these and other embodiments, migration of the device 150 to the valve 156 may be further enhanced by selecting a specific gravity or buoyancy of the device to allow it to move through the stomach contents towards the valve 156.

Figure 15C:
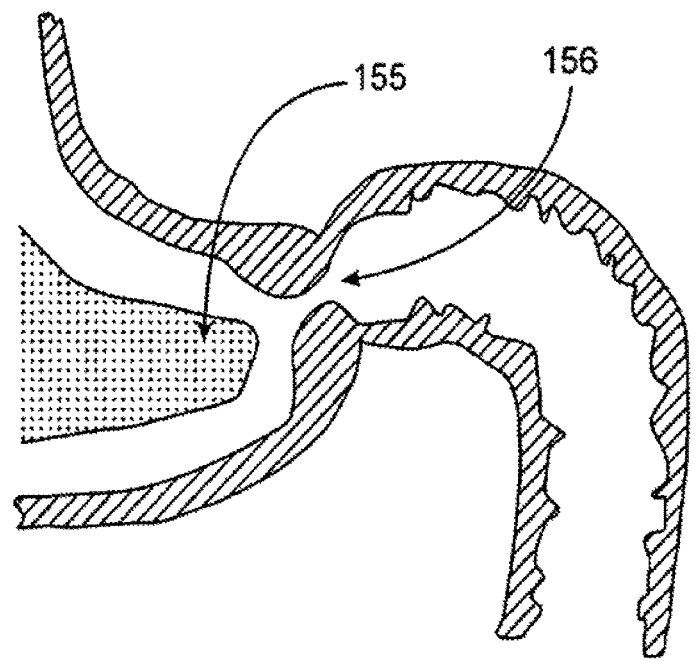
Figure 15D:
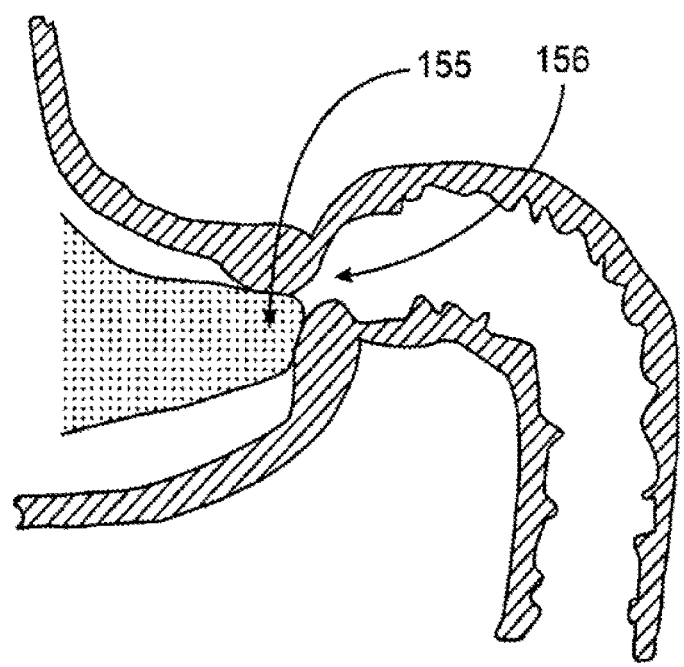

FIGS. 15C and 15D the distal portion 155 of the device 150 in interacting with the pyloric valve 156. As illustrated, the shape of the distal portion 155 is configured to move out of (FIG. 15C) and into (FIG. 15D) contact with the valve 156. This typically occurs during the natural contractions of the stomach, thus providing for intermittent obstruction of the pyloric valve 156. Intermittent obstruction of the pyloric valve 156 causes food in the stomach to be retained longer, and thus, feelings of satiation may be initiated sooner and may last longer, leading the patient to consume less food. In the embodiment shown in FIGS. 15C and 15D, the distal portion 155 fully obstructs the valve 156 when it is in contact. In alternative embodiments, the distal portion 155 may not fully obstruct the valve 156 and may have any of a number of various configurations designed to allow partial flow even when fully contacting the pyloric valve 156. For example, the distal portion 155 may have a shape such as conical, ellipsoid, spherical, pyramidal, tubular, disc-shaped with a protruding member (designed to fit within the pylorus) or the like. In one embodiment, the distal portion 155 and the proximal portion 153 have identical or nearly identical shapes, so that either end may obstruct the pyloric valve 156, regardless of the orientation of the device 150.

The device 150 may have any of a number of additional features for enhancing its delivery into the stomach, it ability to intermittently obstruct the pyloric valve 156, its removal from the stomach and/or the like. In one embodiment, for example, the device 150 includes one or more radiopaque markers, dyes and/or materials for facilitating visualization of the device 150. The device 150 may also include other markers, dyes or materials that enhance its visibility to the naked eye, which may be advantageous in embodiments where the device 150 dissolves and passes through the body or as a safety feature in the unlikely event that the device 150 breaks or ruptures.

In some embodiments, the device 150 may include one or more mechanisms for releasing one or more drugs into the stomach or small intestine beyond the pyloric valve. For example, slow-releasing drugs may be coupled with or infused into materials covering the device 150 or materials used to construct the device 150. These drugs, which may be any of a number of therapeutic or diagnostic agents, may slowly infuse into the patient by drug release into the intestinal tract or through contact with the patient. In other embodiments, the device 150 may incorporate electrical stimulation technologies. For instance, electrical probes may extend from a surface of the device 150 for insertion into the surrounding tissue or electrodes may be formed over a surface of the device 150.

In one embodiment, the device 150 may be covered by an erodable or biodegradable covering for delivery into the stomach. Such a covering may be configured to constrain the device 150, and once the covering comes into contact with substances in the gastric lumen, it may naturally break down and dissolve, thus releasing the device 150 and allowing it to expand. In one embodiment, the device 150 may be covered by different materials each configured to erode at differing rates or in different chemical environments within the stomach.

Figure 16:
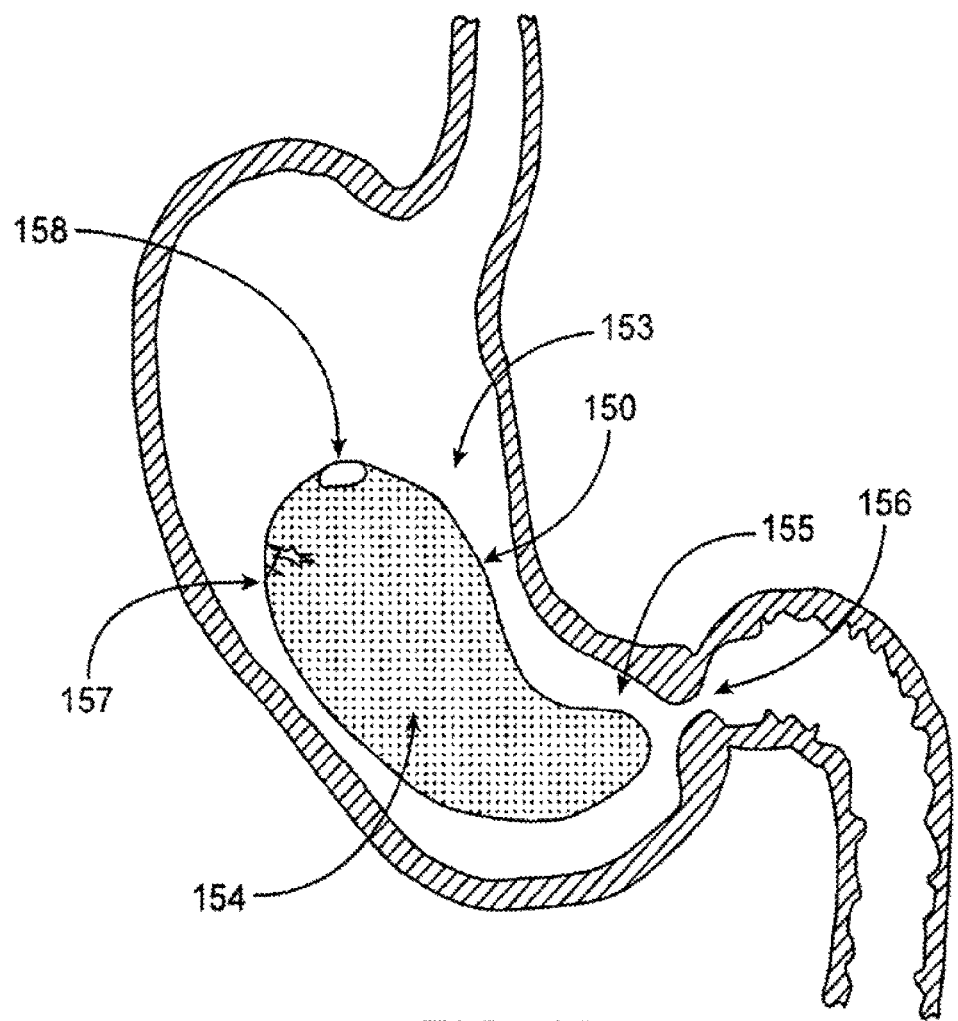
FIG. 16 shows a cross-sectional view of a device as in FIGS. 15A to 15D with a rupture.

FIG. 16 illustrates the device 150 of FIGS. 15A to 15D, in which a rupture 157 has occurred. As demonstrated by this figure, the overall shape of the device 150 is maintained due to expanded foam 154 (or other framework material or the like within or on the device 150 in other embodiments). Generally, the foam or framework material will be acid-resistant in order to prevent its degradation within the stomach and thus allow it to support the device 150 for extended periods of time after rupture has occurred. In an alternative embodiment, the foam 154 or other framework material may degrade slowly after rupture while releasing a signaling material that would alert the patient to the rupture upon examination of feces. The patient would then know to consult his physician to have the device 150 removed.

Figure 17A:
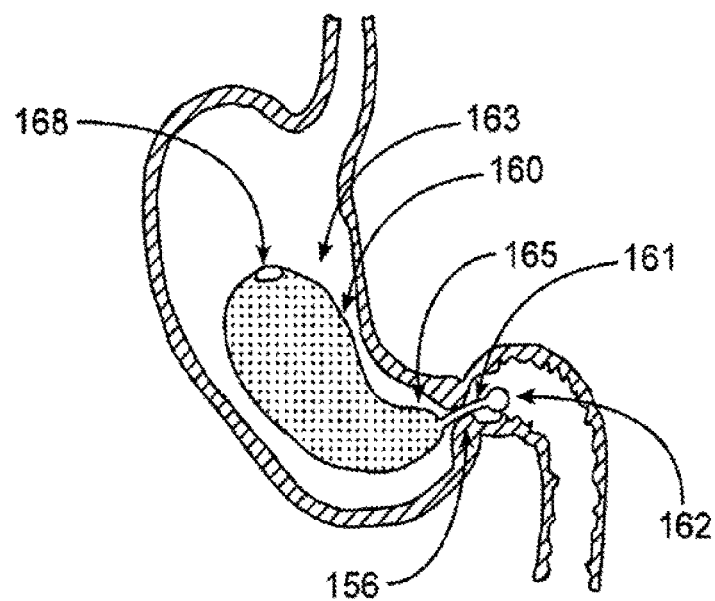
FIG. 17A shows a cross-sectional view of a device having a positioning member and a retaining member, according to one embodiment of the invention.
Figure 17B:
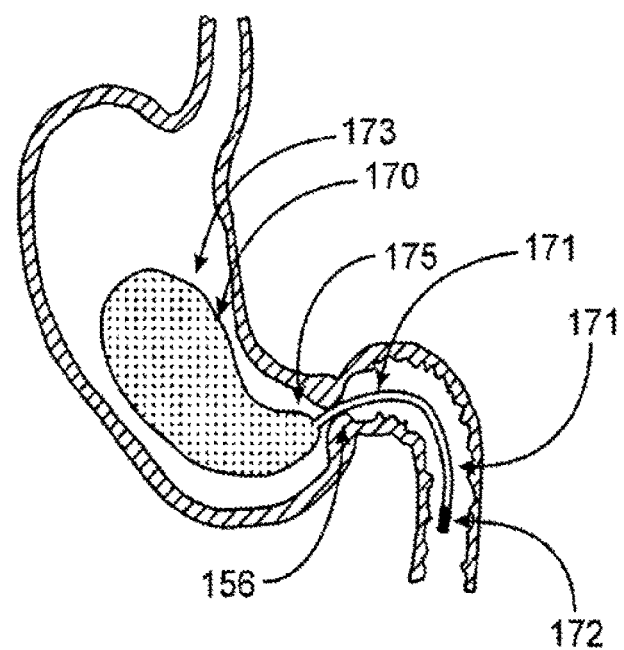
FIG. 17B shows a cross-sectional view of a device having a positioning member with an inflation port, according to one embodiment of the invention.

Referring now to FIGS. 17A and 17B, another embodiment of a pyloric valve obstructing device 160 may include and inflation port 168, a proximal portion 163, a distal portion 165, a positioning member 161 and a retaining member 162. Inflation port 168 is optional, of course, since some embodiments require inflation while others do not. Positioning member 161 generally helps position the device 160 in a location for intermittently obstructing the pyloric valve 156. Retaining member 162 helps maintain the location or position of the device 160.

In one embodiment, the positioning member 161 may be hollow, thus allowing for passage of fluids and/or gases through the device to allow the proximal portion 163, distal portion 165 and retaining member 162 to be inflated. In one embodiment, positioning member 161 may be relatively short, to inhibit movement of the distal portion 165 relative to the pylorus 156. In other embodiments, the positioning member 161 may be longer to allow for more movement of the device 160.

Referring now to FIG. 17B, in another embodiment a device 170 having proximal 173 and distal 175 portions is coupled with a positioning member 171 that includes an inflation port 172 at its distal end. In this embodiment, the device 170 is passed to the stomach in its uninflated state, the positioning member 171 and port 172 are used to inflate the device 170, and the positioning member is then swallowed and passes through the pyloric valve 156 to remain harmlessly in the first part of the small intestine. In another embodiment, the device may be placed into the stomach while attached to a removable tether that extends up the esophagus and into the mouth. The tether can be used to remove the device if it does not properly deploy, or alternatively it can be detached from the device once it is in place in the stomach.

Figure 18A:
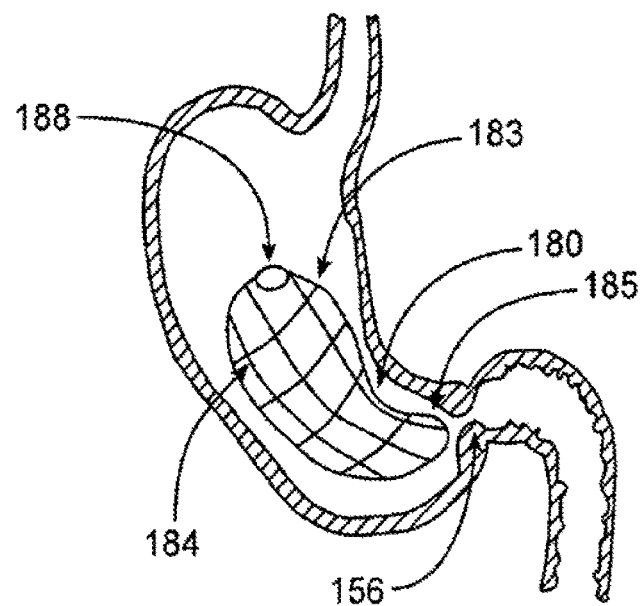
FIGS. 18A and 18B show cross-sectional views of two different embodiments of a device for obstructing a pyloric valve, according to two embodiments.
Figure 18B:
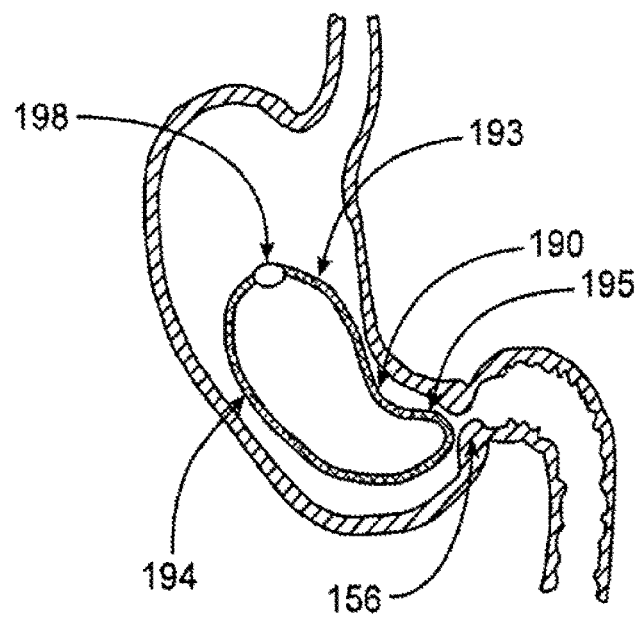

As illustrated in FIGS. 18A and 18B, and as mentioned earlier, various embodiments of a device for obstructing a pyloric valve may include any of a number of different expandable support mechanisms. The embodiments just described included foam, but other supportive structures and materials may be used, such as self-expanding cages, coils, lattices, frameworks or the like. In FIG. 18A, a device 180 having proximal 183 and distal 185 portions as well as an inflation port 188 also includes an expanding scaffolding 184, which may be coupled with the wall of the device 180 on its inner surface or outer surface, or which may be embedded in the wall. Such an expanding scaffolding 184 may be composed of shape memory or super-elastic materials, such as Nitinol. The scaffold 184 may be compressed into a delivery configuration and then either allowed to expand into the desired occlusive shape by self-expansion or expanded by supplying an activation energy, such as, electrical energy, heat, RF energy or the like. In another embodiment, the scaffold may be deployed by pulling the scaffold into an expanded configuration with a pulling device, and in such embodiments the scaffold may have a catch mechanism to prevent it from collapsing to its original shape.

In the embodiment shown in FIG. 18B, a device 190 includes a proximal portion 193, a distal portion 195 and an inflation port 198. In this embodiment, a wall 194 of the device 190 is made of a shape memory, super-elastic or otherwise self-expanding material, which expands from a smaller configuration to a larger configuration upon release from constraint. The material of the wall 194 then retains its expanded shape, thus maintaining the shape of the device 190 and preventing the device from collapsing.

Figure 19B:
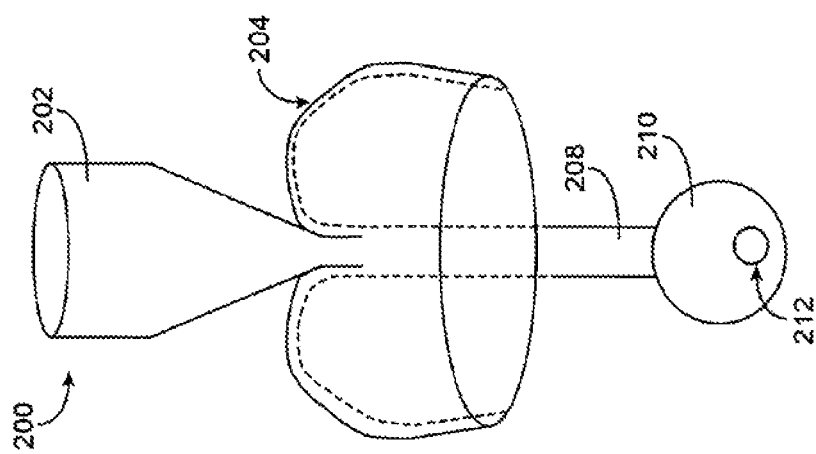
FIGS. 19A and 19B show side views of an device for obstructing a pyloric valve, according to another embodiment.
Figure 19A:
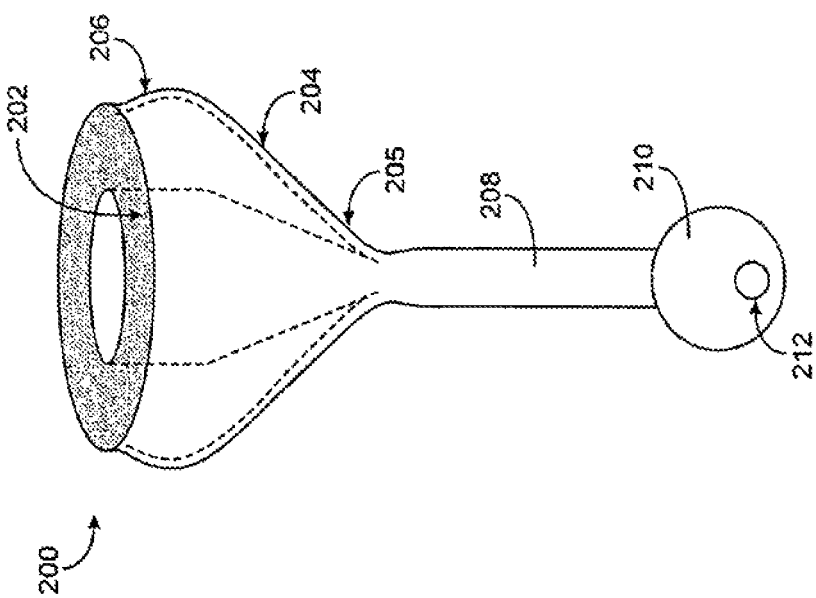

Referring to FIGS. 19A and 19B, another embodiment of a pyloric valve obstructing device 200 includes a movable or "inverted" outer shell 204, an inner core 202, a positioning member 208 and a distal retaining member 210 having a hole 212 or other surface feature. The device 200 is shown in its expanded configuration in FIG. 19A, for intermittently obstructing a pyloric valve, and in its collapsed configuration in FIG. 19B, for delivery into the stomach. The shell 204 includes a tissue contacting/engaging portion 205 and a support portion 206. Generally, the support portion 206 is more rigid/stiffer than the tissue contact portion 205, so that the former helps maintain the cross-sectional diameter of the device 200 so that it cannot pass through the pylorus, while the latter is more compliant so that it can contact stomach tissue without causing significant damage.

The various components of the device 200 may be constructed of any suitable materials, such as those already described or any other suitable materials now known or hereafter discovered. In one embodiment, the inner core 202 is a solid material, such as silicone, but in other embodiments the core 202 may be hollow. The core 202 may have any suitable size, shape, cross-sectional diameter or the like. In one embodiment, the core 202 has a cross-sectional diameter of between about 5 mm and about 30 mm, and preferably about 10 mm. The shell 204 may be made of the same or different material as the core 202, and also may have any suitable size, shape, cross-sectional diameter or the like. In one embodiment, the support portion 206 of the shell 204 is thicker that the tissue contact portion 205. In other embodiments, the support portion 206 may be made of a different material than the tissue contact portion 205.

The positioning member 208 may be an extension of inner core 202, shell 204 or both, or may instead be a separate piece coupled with the inner core 202 and/or outer shell 204. Positioning member 208 may have any suitable length and diameter to allow it to pass through the pyloric valve. In one embodiment its cross-sectional diameter is about 1.0 cm or less and its length is about 3.0 cm or greater. The retaining member 210 may also have any suitable size, shape or configuration, with some embodiments being expandable, some being self-expanding, and others configured to not expand at all. In one embodiment, the retaining member 210 has a greatest cross-sectional diameter of about 30 mm or smaller, and preferably about 25 mm or smaller, and even more preferable about 21 mm or smaller. The hole 212 or surface feature in the retaining member 210 may have any configuration for allowing coupling of an actuator or other device with the retaining member for delivering, adjusting and/or retrieving the device 200. Both the positioning member 208 and the retaining member 210 may be made of any suitable material.

Although not drawn to scale, FIG. 19B illustrates the collapsed or inverted state of the device 200. In this configuration, the shell 204 may be compressed to a smaller cross-sectional diameter for delivery, such as through a delivery tube or catheter. After the device 200 is delivered to the stomach, the shell 204 is inverted to its expanded state and the device 200 may then act to intermittently obstruct the pyloric valve.

FIGS. 20A to 20C illustrate a method for delivering and deploying the device 200 of FIGS. 19A and 19B in a stomach. In FIG. 20A, the device 200 is housed within the lumen of a delivery tube 214 or catheter in its collapsed configuration. In FIG. 20B, the device has been advanced partially out of the delivery tube, allowing the shell 204 to at least partially expand. An actuator 216 hooked through the hole 212 on the retaining member 210 may then be used to pull back on the device 200, such that the shell 204 overlaps the distal end of the delivery tube 214. The distal end of the delivery tube 204 is then used to apply force to the shell 204, causing it to invert into its expanded state, as shown in FIG. 20C. As also shown in FIG. 20C, the actuator 216 may include a hook 218 for coupling with the hole 212 in the retaining member 210. Once the shell 204 is moved to its expanded configuration, it is designed to stay in that configuration, thus providing the pyloric valve contacting and device retention functions described above. In one embodiment, the delivery tube 214 may include an expandable balloon (not shown) at or near its distal end. The balloon maybe doughnut-shaped to inflate circumferentially, or may be have an eccentric shape or any other suitable shape. The balloon may be inflated and serve as a stop against which the device 200 may be pulled. Alternatively, the balloon may be inflated under or within the device 200 to invert the device 200 as the balloon inflates.

In other embodiments, the device may be delivered and/or deployed using any other suitable method. For example, in one embodiment the shell 204 may "self-invert" from its constrained/collapsed state to its expanded state without using an actuator 216 or the distal end of a delivery device 214. Self-inverting may be achieved by shape-memory or spring loaded materials or the like, or by a shell geometry that creates a bias in the stiffness of the device. In another embodiment, the device 200 may be swallowed, either in a folded or otherwise collapsed state or housed within a dissolving caplet. A number of different alternative embodiments are possible.

Figure 21A:
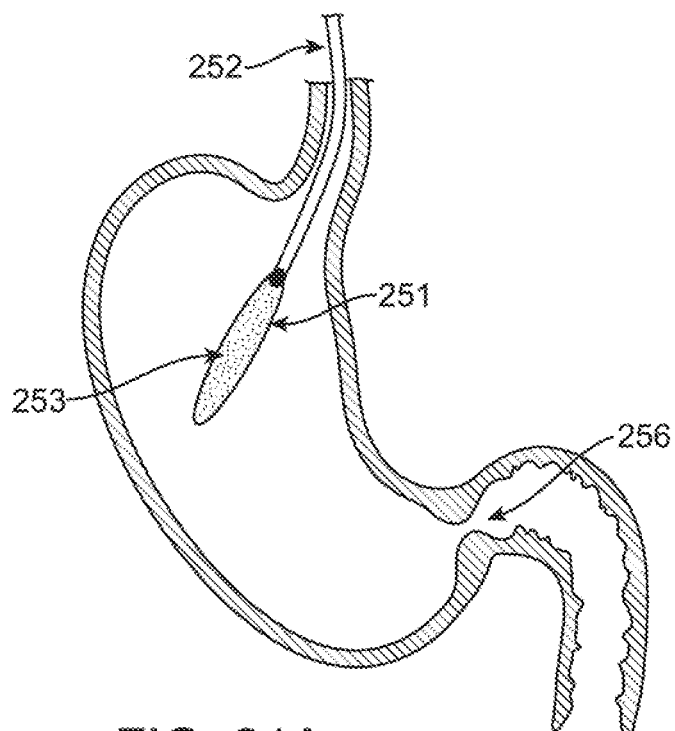
FIGS. 21A and 21B are cross-sectional views of one variation of the device.
Figure 21B:
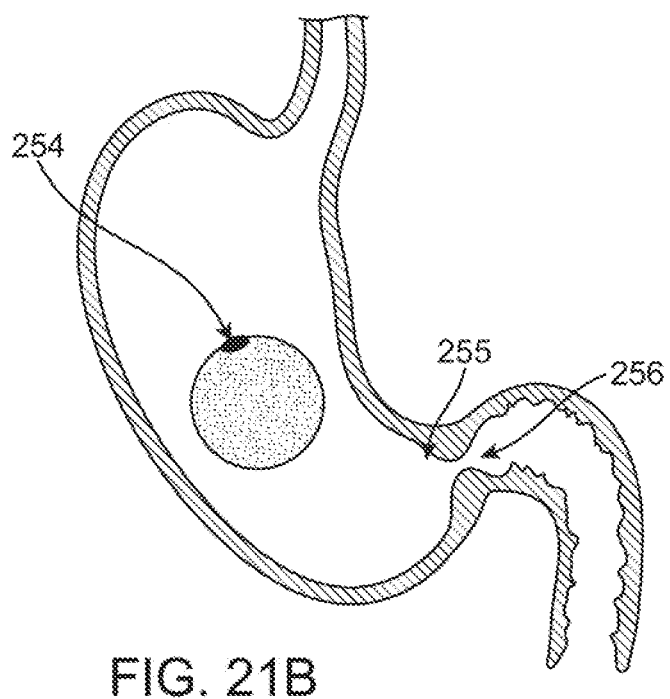

FIGS. 21A and 21B are show the introduction and expansion of one variation of the device. In FIG. 21A, the balloon 251 is introduced by endoscopy tubing 252 in an unexpanded or uninflated state. Inside the balloon is a shape memory foam 253. In FIG. 21B, the balloon 251 is fully inserted and the shape memory foam 253 is expanded according to its shape memory. As noted above, the balloon can be fabricated from silicon, silicon elastomers, latex, polyurethane, PTFE, FEP, or other materials. The interior of the balloon can be a self-expanding material such as a foam or hydrogel that expands upon contact with fluids, such as saline. Alternatively, the balloon can be expanded by being filled with any nontoxic liquid or gas, through an inflation port 254. The distal occlusive portion 255 of the balloon will occlude the pyloric valve 256.

Figure 22A:
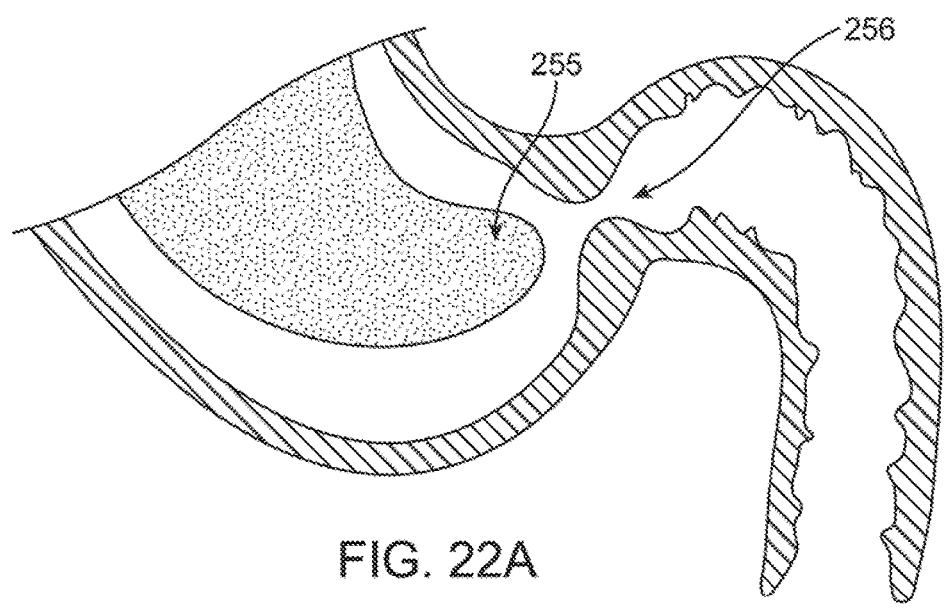
FIGS. 22A and 22B are close-up views of the device, with FIG. 22A showing the device close to but not obstructing the pylorus and FIG. 22B showing the device obstructing the pylorus.
Figure 22B:
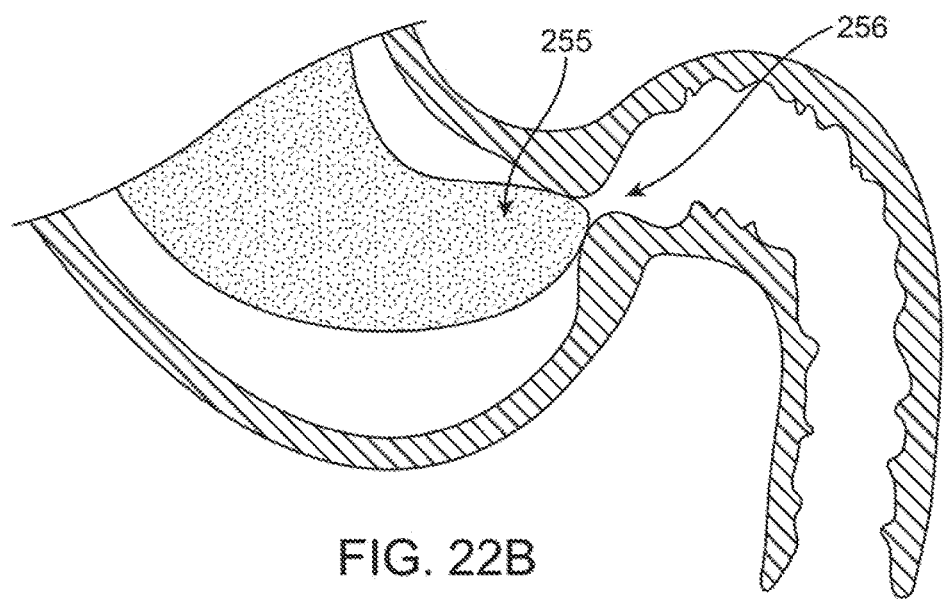
Figure 23:
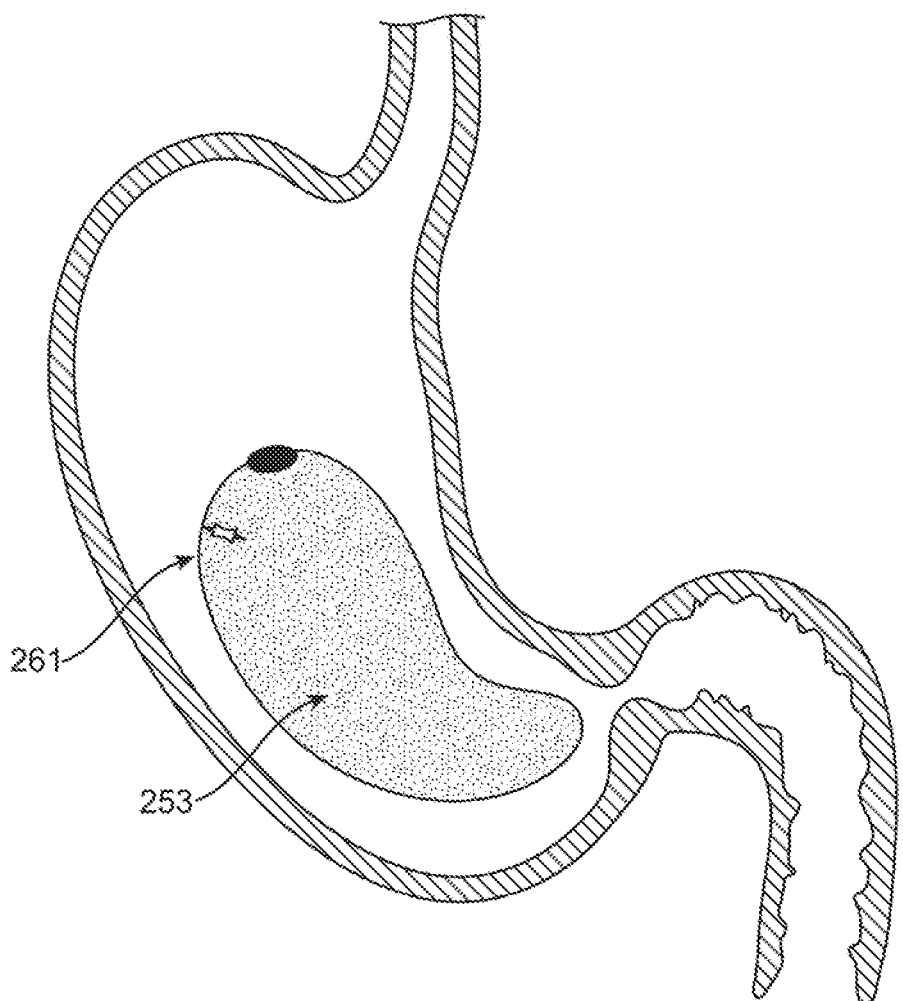
FIG. 23 shows retention of the device after an accidental rupture in vivo.

In FIGS. 22A and 22B, the occlusion portion 255 is shown in two successive positions moving into engagement with the pyloric valve 256. A visible dye or marker, preferably one that is highly visible, can be infused into the balloon 251 as a safety measure. Alternatively, the balloon itself can be fabricated from a material that is highly visible and visually distinct from tissue so that in the unlikely event of a rupture of the balloon, the due or pieces of the balloon will become visible as they pass from the body, indicating to the patient or to a physician that a rupture has occurred.

The balloon can also be covered by an erodible or biodegradable covering that will constrain the balloon until the balloon is ingested or placed within the gastric lumen where the gastric fluids will erode the covering and thereby allow the balloon to expand or inflate. The balloon can also be covered with materials that are configured to erode at differing rates or in different environments.

In FIG. 3, a rupture 261 has occurred in the balloon 253 and yet the profiled of the balloon is maintained due to the shape memory foam or expansile internal material retained inside the balloon. The foam or material is preferably acid-resistant to prevent degradation and allow it to support the balloon wall for extended periods of time following rupture. Alternatively, the balloon filling could degrade slowly after rupture with release of a signaling material to alert the patient to its rupture upon examination of feces.

Figure 24A:
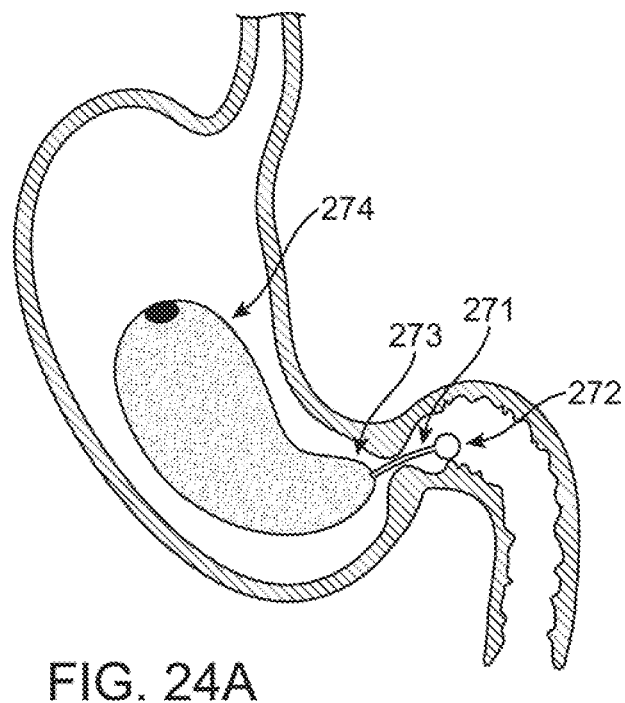
FIG. 24A is a cross sectional view of the device with an anchoring intestinal bulb.

In FIG. 24A, a pylorus-spanning tether 271 is attached to the balloon, and a distal occluding member 272 is attached to the opposite end of the tether 271. The tether 271 holds the distal end 273 of the balloon 274 near the pylorus to urge the balloon toward the position in which it obstructs the pylorus. A relatively short tether 271 will limit the range of movement of the occlusive (distal) end 273 of the balloon relative to the pylorus.

Figure 24B:
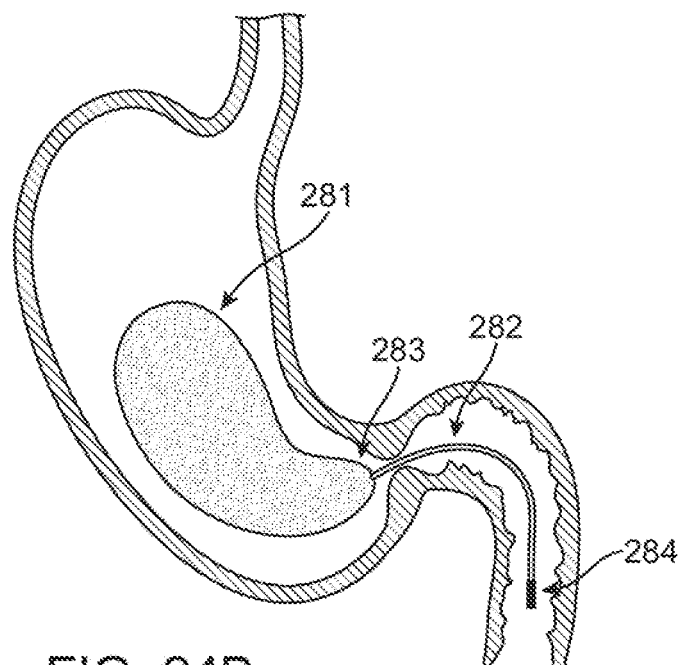
FIG. 24B is a cross-sectional view of the device with anchoring intestinal tubing and a distal inflation port.

In FIG. 24B, the balloon 281 has a tether 282 attached to its distal end 283 and an inflation port 284 at the distal end of the tether 282. To utilize this device, the balloon 281 is swallowed without swallowing the inflation port 284, leaving the inflation port inside the patient's mouth. Once the balloon has been inflated through the inflation port, the patient can simply ingest the tether 282 which will eventually migrate across the pyloric valve 285 and help hold the distal end 283 of the balloon in the region of the pyloric valve.

Figure 25A:
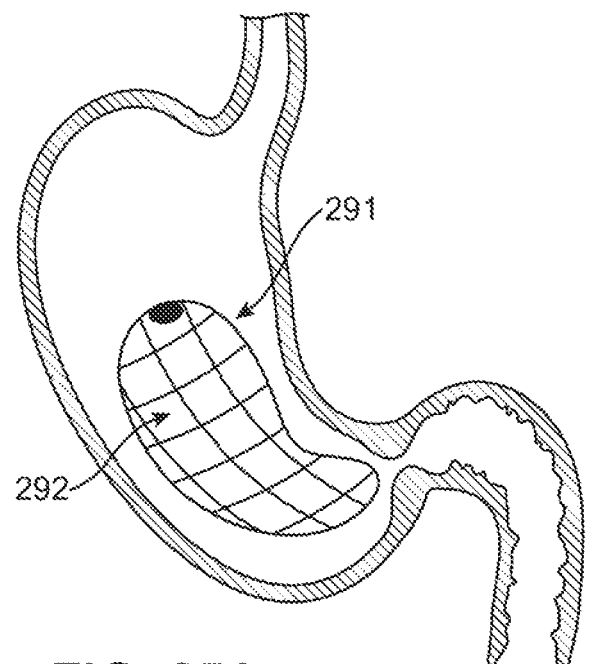
FIG. 25A is a cross sectional view of the device with supportive internal caging.
Figure 25B:
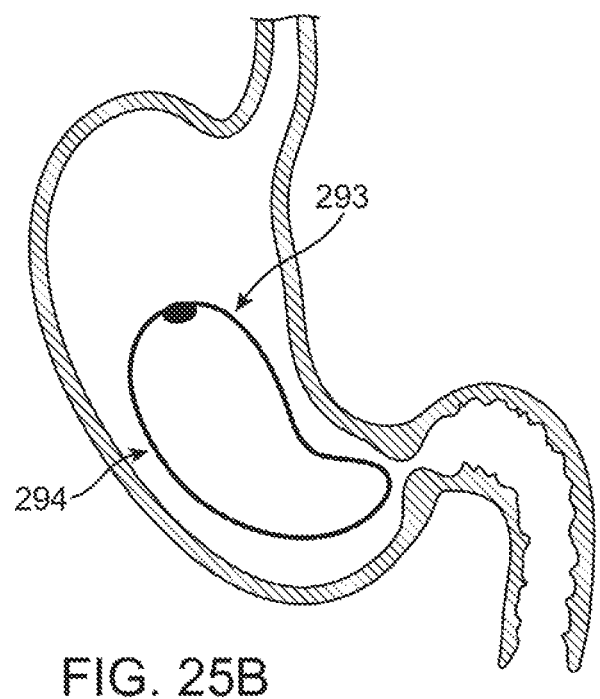
FIG. 25B is a cross sectional view of the device with a shape memory external shell.

Further variations are shown in FIGS. 25A and 25B. In FIG. 25A, the balloon 291 contains internal expandable caging 292 to establish its shape, while in FIG. 25B, the balloon 293 contains an outer shell 294 made of a shape memory material.

Figure 26A:
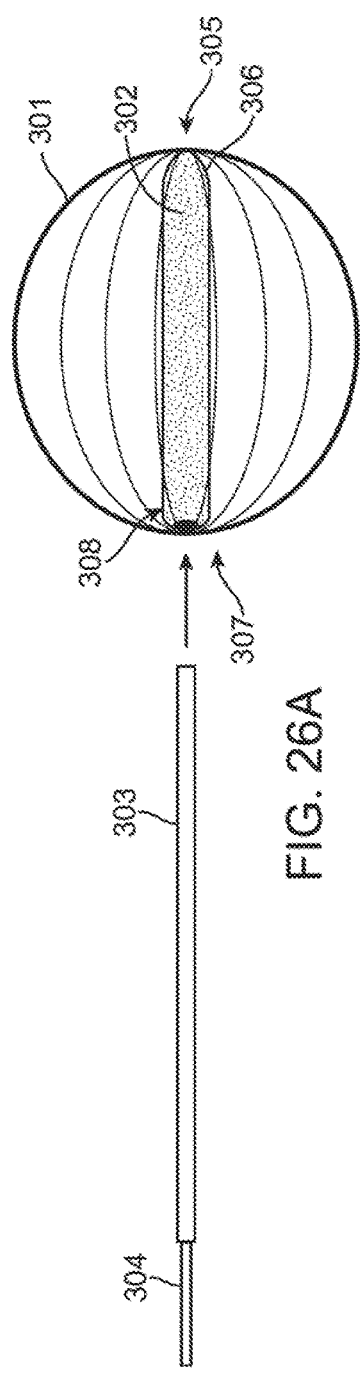
FIGS. 26A, 26B, and 26C illustrate a device within the scope of the invention, that supports and retains a functional component such as a gastric volume reducer, a drug pump or a gastric stimulator inside the stomach without obstructing the pylorus, and can be inserted and removed at will by a physician.
Figure 26B:
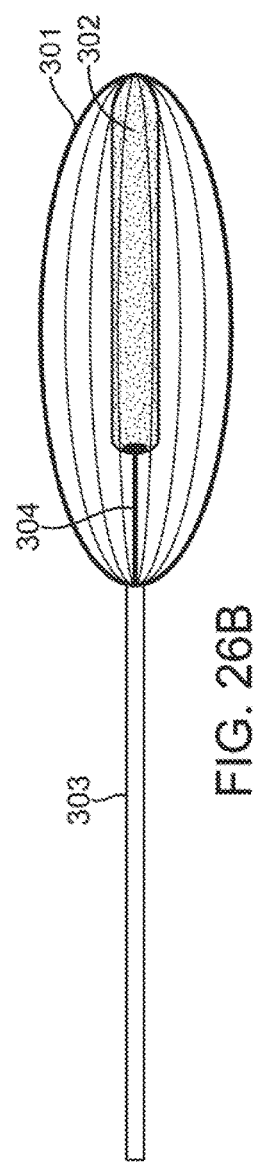
Figure 26C:
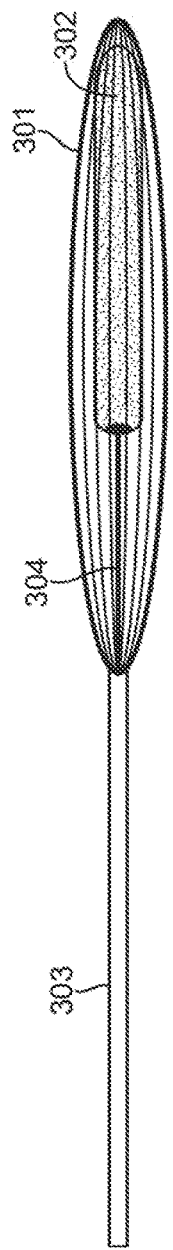

A still further variation on the device and its use are shown in FIGS. 26A, 26B, and 26C. The device in these figures is a shape-memory component 301 such as a resilient lattice or cage, with a functional component 302 held inside. In its relaxed position, the shape-memory component 301 is large in volume, shown here as a sphere (FIG. 26A), that cannot pass through the pylorus and is therefore retained in the stomach but of open structure to avoid any interference with the flow of digested matter from the stomach through the pylorus into the intestine. The shape-memory component 301 can also be elongated to a deformed position, as shown in FIG. 26C, by applying and maintaining a longitudinal extension force to the component. In this deformed position, the device can be inserted into the stomach through the esophagus. The functional component 302 fits inside the shape-memory component 301 in both the relaxed and elongated conformations of the shape-memory component. The functional component 302 is either a drug pump, a gastric stimulator, or any other delivery or otherwise therapeutic device. Manipulation of the shape-memory component 301 is achieved by an endoscopic tool 303 that contains an internal extension rod 304 that can be moved forward and back relative to the tool by standard external means (not shown) that are common and known for endoscopy tools. The distal ends of both the endoscopy tool 303 and the extension rod 304 can be fined with grasping components such as forceps, a snare, or the like. To insert the device into the stomach of a patient, a physician will mount the device to the distal end of the endoscopy tool, with the distal end of the tool attached to the proximal end of the shape memory device 301 and the distal end of the internal rod attached to the proximal end of the functional component 302. The physician will then extend the rod 304 to elongate the shape memory component 301 as in FIG. 26C, thereby reducing its diameter so that the entire device can be inserted into the stomach. Once inserted, the rod 304 is retracted by the physician, through an intermediate configuration as in FIG. 26B to a relaxed configuration as in FIG. 26A. Removal of the device from the stomach is achieved by the reverse procedure, i.e., the endoscopy tool 303 with retracted rod 304 is inserted into the stomach (through the esophagus) and once inserted, its grasping components are manipulated to engage the components of the device. Once these components are engaged, the rod is extended, causing elongation and deformation of the shape memory component and thereby enabling removal of the entire device from the stomach.

In a further variation on the device pictured in FIGS. 26A, 26B, and 26C, the shape-memory component 301 is replaced with a relatively flexible cage of the same configuration, either without a shape memory or with a shape memory that is less than fully realized after distortion. The distal end 305 of the cage is joined to the distal end 306 of the functional component, while the proximal ends 307, 308, respectively, are joinable but detachable, i.e., reversibly joinable. When the proximal ends 307, 308 are joined, as shown in FIG. 26A, the cage 301 is fixed in the configuration shown and thereby retainable in the stomach due to its large diameter. When the proximal ends are detached, the cage 301 and functional component 302 are removable, insertable, or generally capable of manipulation. Engagement and disengagement of the proximal ends can be achieved by endoscopy tools, such as forceps, gasping elements for twisting, or cutting elements. In certain embodiments, labels that are detectable and capable of being monitored from outside the body are affixed to the proximal end of the functional device 302, the cage 301, or both, to facilitate the manipulations.

In still further embodiments, the shape memory component or flexible cage 301 is useful by itself, i.e., without the presence of an additional functional component 302, as a space-occupying device to reduce the volume in the stomach. This serves as a means of weight reduction by reducing the volume of food that can be retained in the stomach and thereby the volume that can be absorbed through the stomach walls.

Although the above is a complete and accurate description of the invention, any of a number of variations, additions and the like may be made to the embodiments described without departing from the scope of the invention. For example, devices and methods described above are not limited strictly to treatment of obesity, but may also be used to treat other conditions. Furthermore, other devices, such as imaging devices, chemical detection devices, space occupying devices and/or the like may be incorporated into many of the embodiments described above without departing from the scope of the invention. Therefore, the foregoing description is provided primarily for exemplary purposes and should not be interpreted to limit the scope of the invention as it is defined in the following claims.

We claim:

1. A method of occupying a volume within a stomach, comprising:
    per-orally introducing an obstructive device into the stomach via an elongate delivery instrument, the obstructive device having a bridging member with a first balloon and a second balloon each attached to the bridging member which has a diameter sufficient to maintain each balloon in proximity to one another;
    introducing a fluid through the delivery instrument and through the bridging member coupled to the delivery instrument, wherein introducing the fluid comprises introducing the fluid through at least one fluid lumen defined through the bridging member via a fluid inflation port, wherein the fluid inflation port is positioned on the first balloon and wherein the fluid inflation port is entirely within the stomach when the obstructive device is introduced into the stomach, wherein the first balloon and the second balloon inflate sequentially within the stomach to a deployment configuration where each balloon has a rounded configuration; and
    decoupling the delivery instrument from the bridging member such that the obstructive device remains in the stomach, wherein the first balloon and the second balloon are free to move within the stomach, and movement of the balloons relative to the stomach is restricted via contact with stomach tissue.

2. The method of claim 1 further comprising visualizing the obstructive device while introducing the fluid.

3. The method of claim 1 wherein the first balloon is comprised of a first material which is different from a second material comprising the second balloon.

4. The method of claim 1 wherein the fluid inflation port is self-sealing.

5. The method of claim 1 further comprising restricting passage of food through the stomach via intermittent contact between the obstructive device and the stomach tissue.

6. The method of claim 1 further comprising rupturing at least one of the balloons.

7. The method of claim 6 further comprising per-orally removing the obstructive device from the stomach.

8. A method of occupying a volume within a stomach, comprising:
    deploying an obstructive device within the stomach, the obstructive device having a bridging member with a first balloon and a second balloon each attached to the bridging member which has a diameter sufficient to maintain each balloon in proximity to one another, wherein the first balloon and the second balloon are inflated sequentially by fluid introduced through a delivery instrument and through the bridging member coupled to the delivery instrument, wherein introducing the fluid comprises introducing the fluid through at least one fluid lumen defined through the bridging member via a fluid inflation port, wherein the fluid inflation port is positioned on the first balloon and wherein the fluid inflation port is entirely within the stomach when the obstructive device is introduced into the stomach, and wherein the balloons are inflated within the stomach to a deployment configuration where each balloon has a rounded configuration;
    decoupling the delivery instrument from the bridging member such that the obstructive device remains in the stomach, wherein the first balloon and the second balloon are free to move within the stomach, and movement of the balloons relative to the stomach is restricted via contact with stomach tissue;
    visualizing the obstructive device positioned within the stomach;
    rupturing at least one of the balloons such that the balloons deflate; and
    per-orally removing the obstructive device from the stomach.

9. The method of claim 8 wherein the obstructive device is visualized while introducing the fluid.

10. The method of claim 8 wherein the first balloon is comprised of a first material which is different from a second material comprising the second balloon.

11. The method of claim 8 wherein the fluid inflation port is self-sealing.

12. The method of claim 8 further comprising restricting passage of food through the stomach via intermittent contact between the obstructive device and the stomach tissue prior to rupturing at least one of the balloons.

13. The method of claim 1, wherein at least one of the first balloon and the second balloon is substantially spherical when inflated into the deployment configuration.

14. The method of claim 8, wherein at least one of the first balloon and the second balloon is substantially spherical when inflated into the deployment configuration.

15. A method of occupying a volume within a stomach, comprising:
    per-orally introducing an obstructive device into the stomach via an elongate delivery instrument, the obstructive device having a bridging member with a first balloon and a second balloon each attached to the bridging member which has a diameter sufficient to maintain each balloon in proximity to one another;
    introducing a fluid through the delivery instrument and through the bridging member coupled to the delivery instrument, wherein the first balloon and the second balloon inflate sequentially within the stomach to a deployment configuration, and wherein at least one of the first balloon and the second balloon is substantially spherical when inflated into the deployment configuration; and
    decoupling the delivery instrument from the bridging member such that the obstructive device remains in the stomach, wherein the first balloon and the second balloon are free to move within the stomach, and movement of the balloons relative to the stomach is restricted via contact with stomach tissue.

16. A method of occupying a volume within a stomach, comprising:
    deploying an obstructive device within the stomach, the obstructive device having a bridging member with a first balloon and a second balloon each attached to the bridging member which has a diameter sufficient to maintain each balloon in proximity to one another, wherein the first balloon and the second balloon are inflated sequentially by fluid introduced through a delivery instrument and through the bridging member coupled to the delivery instrument, wherein the balloons are inflated within the stomach to a deployment configuration, and wherein at least one of the first balloon and the second balloon is substantially spherical when inflated into the deployment configuration;

decoupling the delivery instrument from the bridging member such that the obstructive device remains in the stomach, wherein the first balloon and the second balloon are free to move within the stomach, and movement of the balloons relative to the stomach is restricted via contact with stomach tissue;

visualizing the obstructive device positioned within the stomach;

rupturing at least one of the balloons such that the balloons deflate; and per-orally removing the obstructive device from the stomach.

* * * * *